(12) United States Patent
Fäcke et al.

(10) Patent No.: US 10,329,244 B2
(45) Date of Patent: Jun. 25, 2019

(54) MOISTURE-STABLE HOLOGRAPHIC MEDIA

(71) Applicant: Covestro Deutschland AG, Leverkusen (DE)

(72) Inventors: Thomas Fäcke, Leverkusen (DE); Friedrich-Karl Bruder, Krefeld (DE); Thomas Rölle, Leverkusen (DE); Dennis Hönel, Züpich-Wichterich (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/536,841

(22) PCT Filed: Dec. 11, 2015

(86) PCT No.: PCT/EP2015/079385
§ 371 (c)(1),
(2) Date: Jun. 16, 2017

(87) PCT Pub. No.: WO2016/096641
PCT Pub. Date: Jun. 23, 2016

(65) Prior Publication Data
US 2017/0362165 A1 Dec. 21, 2017

(30) Foreign Application Priority Data

Dec. 19, 2014 (EP) ..................... 14199164

(51) Int. Cl.
*G03H 1/02* (2006.01)
*G03F 7/027* (2006.01)
(Continued)

(52) U.S. Cl.
CPC .......... *C07C 229/40* (2013.01); *C07C 271/26* (2013.01); *C07C 271/28* (2013.01);
(Continued)

(58) Field of Classification Search
None
See application file for complete search history.

(56) References Cited

U.S. PATENT DOCUMENTS 4,250,322 A * 2/1981 Efimov ................... C08F 20/36
560/115
4,965,152 A * 10/1990 Keys ...................... G02B 5/203
359/15

(Continued)

FOREIGN PATENT DOCUMENTS

CN 104371088 * 2/2015 ............. C08G 18/62
CN 104371088 A 2/2015
(Continued)

OTHER PUBLICATIONS

Machine translation of CN 104371088 (2015).*
(Continued)

*Primary Examiner* — Martin J Angebranndt
(74) *Attorney, Agent, or Firm* — Drinker Biddle & Reath LLP

(57) ABSTRACT

The invention relates to novel compounds which are especially suitable for use as writing monomers in holographic media. The invention further provides a photopolymer and a holographic medium comprising the inventive compounds, and an optical display, a security document and a holographic optical element comprising an inventive holographic medium.

13 Claims, 4 Drawing Sheets

Figure 1:
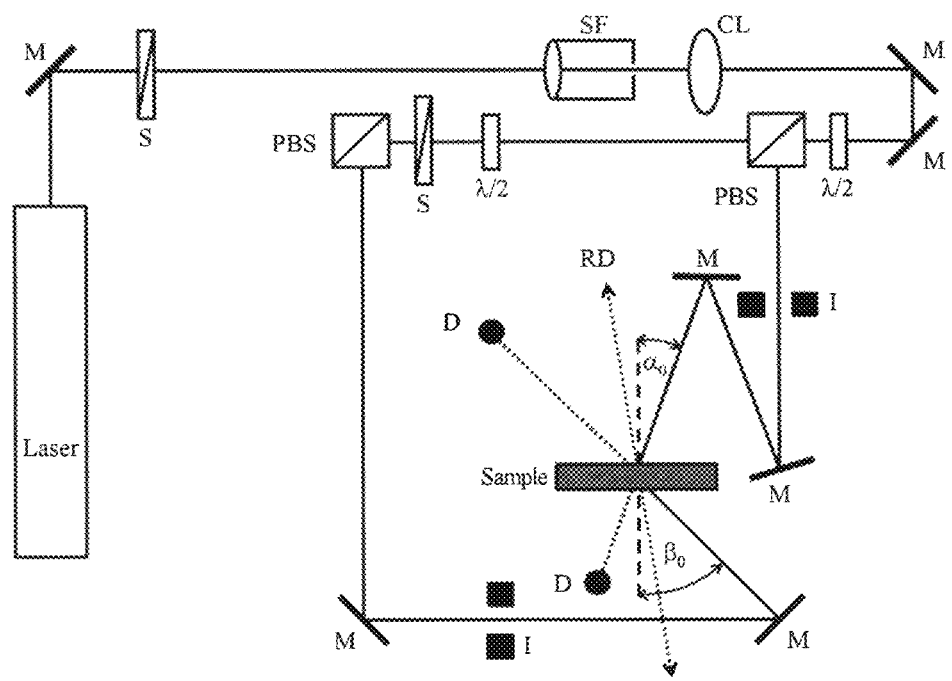

(51) Int. Cl.
- *G03F 7/035* (2006.01)
- *G03F 7/004* (2006.01)
- *C07C 229/40* (2006.01)
- *C07C 271/28* (2006.01)
- *C07C 323/43* (2006.01)
- *G03F 7/00* (2006.01)
- *G03H 1/00* (2006.01)
- *C07C 271/26* (2006.01)
- *G03H 1/04* (2006.01)

(52) U.S. Cl.
CPC .......... *C07C 323/43* (2013.01); *G03F 7/001* (2013.01); *G03F 7/0046* (2013.01); *G03F 7/027* (2013.01); *G03F 7/035* (2013.01); *G03H 1/0011* (2013.01); *G03H 1/0248* (2013.01); *G03H 2001/0264* (2013.01); *G03H 2001/0415* (2013.01); *G03H 2260/12* (2013.01); *G03H 2260/31* (2013.01)

(56) References Cited

U.S. PATENT DOCUMENTS

| | | | | |
|---|---|---|---|---|
| 7,271,283 | B2* | 9/2007 | Chisholm | C07C 323/12 |
| | | | | 560/121 |
| 8,222,314 | B2 | 7/2012 | Roelle et al. | |
| 8,999,608 | B2* | 4/2015 | Rolle | C08G 18/2885 |
| | | | | 359/3 |
| 9,098,065 | B2 | 8/2015 | Honel et al. | |
| 9,146,456 | B2 | 9/2015 | Berneth et al. | |
| 9,156,931 | B2* | 10/2015 | Kobayashi | G02B 1/04 |
| 2010/0036013 | A1 | 2/2010 | Roelle et al. | |
| 2012/0062658 | A1 | 3/2012 | Koseki | |
| 2012/0214089 | A1* | 8/2012 | Honel | G03H 1/02 |
| | | | | 430/2 |
| 2012/0219884 | A1* | 8/2012 | Weiser | G03F 7/001 |
| | | | | 430/2 |
| 2012/0219885 | A1* | 8/2012 | Facke | C07C 271/30 |
| | | | | 430/2 |
| 2012/0237856 | A1* | 9/2012 | Rolle | G03F 7/001 |
| | | | | 430/2 |
| 2012/0302659 | A1* | 11/2012 | Rolle | G03F 7/001 |
| | | | | 522/173 |
| 2013/0177746 | A1* | 7/2013 | Facke | B32B 27/40 |
| | | | | 428/195.1 |
| 2013/0209922 | A1* | 8/2013 | Masunaga | G03F 7/0382 |
| | | | | 430/5 |
| 2013/0252140 | A1* | 9/2013 | Facke | C07C 323/12 |
| | | | | 430/2 |
| 2016/0279033 | A1* | 9/2016 | Moser | C07C 271/28 |
| 2017/0363957 | A1* | 12/2017 | Roelle | G03F 7/028 |

FOREIGN PATENT DOCUMENTS

| | | | | |
|---|---|---|---|---|
| EP | 0223587 | A1 | 5/1987 | |
| EP | 1676870 | * | 7/2006 | ............ C08F 220/18 |
| EP | 2154128 | A1 | 2/2010 | |
| EP | 2354845 | * | 2/2010 | ............ G03F 7/027 |
| EP | 2450387 | A1 | 5/2012 | |
| JP | 02-150410 | * | 6/1990 | ............ G02B 1/04 |
| JP | 04-091114 | * | 3/1992 | ............ C08F 299/08 |
| JP | 05-027434 | * | 2/1993 | ............ G03F 7/004 |
| JP | 2003-012727 | * | 1/2003 | ............ G02B 1/04 |
| WO | 2004/077511 | * | 9/2004 | |
| WO | WO-2012062655 | A2 | 5/2012 | |

OTHER PUBLICATIONS

Machine transdlatiuon of EP 2354845 (Oct. 2011).*
International Prelminary Report on Patentability for PCT/EP2015/079385 with Written Opinion of the International Searching Authority dated Jun. 29, 2017.
International Search Report for PCT/EP2015/079385 dated Feb. 19, 2016.
Written Opinion of the International Searching Authority for PCT/EP2015/079385 dated Feb. 19, 2016 (in German).
Database CA [Online] Chemical Abstracts Service, Columbus, Ohio, US; NIE, Jun et el.; "Preparation method of polyurethane acrylate with high wear and heat resistance", XP002738918, retrieved from STNDatabase accession No. 20152738918.

* cited by examiner

MOISTURE-STABLE HOLOGRAPHIC MEDIA

CROSS-REFERENCE TO RELATED APPLICATIONS

This application is a national stage application (under 35 U.S.C. § 371) of PCT/EP2015/079385, filed Dec. 11, 2015, which claims the benefit of European Application No. 14199164.6, filed Dec. 19, 2014, both of which are incorporated herein by reference in their entirety.

The invention relates to novel compounds which are especially suitable for use as writing monomers in holographic media. The invention further provides a photopolymer and a holographic medium comprising the inventive compounds, and an optical display, a security document and a holographic optical element comprising an inventive holographic medium.

BACKGROUND OF THE INVENTION

For the uses of photopolymers for the production of holographic media, the crucial role is played by the refractive index constant Δn produced in the photopolymer by the holographic exposure. In holographic exposure, the interference field of signal light beam and reference light beam (that of two planar waves in the simplest case) is mapped into a refractive index grating by the local photopolymerization of, for example, high-refractive acrylates at loci of high intensity in the interference field. It is the refractive index grating in the photopolymer which is the hologram and which contains all the information in the signal light beam. By illuminating the hologram with only the reference light beam, the signal can then be reconstructed. The strength of the signal thus reconstructed relative to the strength of the incident reference light is called the diffraction efficiency, DE in what follows.

High-refractive acrylates are capable of producing refractive index gratings with high amplitude between regions with low refractive index and regions with high refractive index, and hence of enabling holograms with high DE and high Δn in the photopolymer. It should be noted here that the grating thickness and hence the DE depends on the product of Δn and the photopolymer layer thickness d. The breadth of the angle range at which the hologram becomes visible (is reconstructed), for example under monochromatic illumination, then depends solely on the layer thickness d. On illumination of the hologram with white light, for example, at a given illumination angle, the breadth of the spectral range which can contribute to the reconstruction of the hologram likewise depends solely on the layer thickness d. The smaller d is, the greater the respective breadths of acceptance. Therefore, if the intention is to produce bright and readily visible holograms, the aim is a high Δn and a low thickness d, so as to maximize DE. This means that, the higher the Δn, the more freedom is achieved to configure the layer thickness d for bright holograms without loss of DE. Therefore, the optimization of Δn is of major importance in the optimization of photopolymers (P. Hariharan, Optical Holography, 2nd Edition, Cambridge University Press, 1996).

WO 2010/0036013 discloses writing monomers based on (substituted) phenylcarbamoyloxyethyl propenonates and the use thereof as writing monomers in photopolymers for production of holographic media. It is possible to write holograms into these media with high diffraction efficiencies (DE).

However, the known holographic media do not have sufficiently high stability to varying humidity conditions for all applications. For instance, the optical function of exposed media changes considerably in some cases depending on the humidity that exists in each case. The effect of this is that the holographic media can reliably fulfil their optical function only within a tightly defined humidity range. Conversely, they lose their function entirely or at least partly when they are used in an environment in which the humidity level is outside the tight specified range.

BRIEF SUMMARY OF THE INVENTION

The problem addressed the present invention was therefore that of providing compounds for the production of holographic media, the use of which firstly enables the writing of holograms having a high refractive index contrast (Δn) of more than 0.025 and secondly considerably reduces the influence of varying humidity conditions on the reconstruction wavelength. More particularly, the media, under varying ambient humidities, should have a maximum change in the reconstruction wavelength of less than 5 nm based on a reflection hologram which has been written by interference of two planar waves having a wavelength of 532 nm.

This problem is solved by the compound of formula (I)

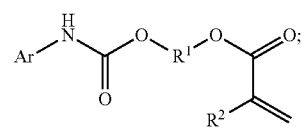

in which
R$^1$ is an aliphatic hydrocarbyl radical having 1-8 carbon atoms;
R$^2$ is hydrogen or methyl;
Ar is an aromatic radical of the formula (II)

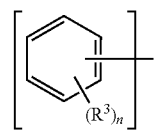

in which
R$^3$ are independently radicals selected from the group of substituted or unsubstituted phenyl, substituted or unsubstituted phenylthiyl, branched or unbranched alkyl, branched or unbranched alkylthiyl, halogen, where at least one of the R$^3$ radicals is a radical selected from the group of substituted or unsubstituted phenyl, substituted or unsubstituted phenylthiyl;
n=1 or 5;
or Ar is an aromatic radical of the formula (III)

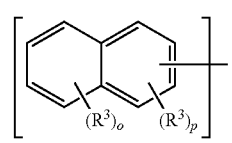

in which
R$^3$ are independently radicals selected from the group of substituted or unsubstituted phenyl, substituted or unsubstituted phenylthiyl, branched or unbranched alkyl, branched or unbranched alkylthiyl, halogen, where at least one of the $R^3$ radicals is a radical selected from the group of substituted or unsubstituted phenyl, substituted or unsubstituted phenylthiyl;

o=1 to 3;
p=1 or 4, wherein the compound of the formula (I) has only one radiation-curing group.

The problem is additionally solved by the compound of formula (I')

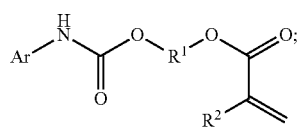

in which
$R^1$ is an aliphatic hydrocarbyl radical having 1-8 carbon atoms;
$R^2$ is hydrogen or methyl;
Ar is an aromatic radical of the formula (II')

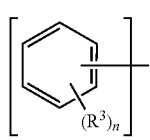

in which
$R^{3'}$ are independently radicals selected from the group of unsubstituted phenyl, substituted or unsubstituted phenylthiyl, branched or unbranched alkyl, branched or unbranched alkylthiyl, halogen, where at least one of the $R^{3'}$ radicals is a radical selected from the group of substituted or unsubstituted phenyl, substituted or unsubstituted phenylthiyl;

n=1 to 5;

or Ar is an aromatic radical of the formula (III)

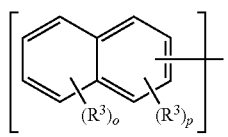

in which
$R^3$ are independently radicals selected from the group of substituted or unsubstituted phenyl, substituted or unsubstituted phenylthiyl, branched or unbranched alkyl, branched or unbranched alkylthiyl, halogen, where at least one of the $R^3$ radicals is a radical selected from the group of substituted or unsubstituted phenyl, substituted or unsubstituted phenylthiyl;

o=1 to 3;
p=1 to 4, wherein the compound of the formula (I') has only one radiation-curing group, Thus, it has been found that, surprisingly, it is possible with the aid of the inventive compounds to obtain holographic media which, in the exposed state, function in a manner unaffected, or affected only to a minor degree, even under varying conditions, particularly under varying humidity conditions. These media additionally have a high refractive index contrast (Δn).

DETAILED DESCRIPTION OF THE INVENTION

According to the invention, radiation-curing groups refer to those functional groups which can be free-radically polymerized in the presence of initiator radicals produced by the action of actinic radiation. Examples of radiation-curing groups are the acrylate and methacrylate groups.

The inventive compounds can be prepared, for example, by urethanization of an appropriately substituted phenyl isocyanate with a hydroxyalkyl acrylate. The urethanization can be conducted at 60-120° C. using a urethanization catalyst.

Suitable catalysts are tertiary amines, tin compounds, zinc compounds, iron compounds or bismuth compounds, especially triethylamine, 1,4-diazabicyclo-[2.2.2]-octane, bismuth octoate or dibutyltin dilaurate. The urethane acrylates obtained may have a content of free residual monomers of less than 0.5% by weight, preferably less than 0.2% by weight, more preferably less than 0.1% by weight, based on the urethane acrylate. The urethanization can be conducted in a non-reactive solvent, for example an aromatic or aliphatic hydrocarbon or an aromatic or aliphatic halogenated hydrocarbon or a paint solvent, for example ethyl acetate or butyl acetate or acetone or butanone or an ether such as tetrahydrofuran or tertbutyl methyl ether or a dipolar aprotic solvent such as dimethyl sulphoxide or N-methylpyrrolidone or N-ethylpyrrolidone.

The phenylurethane acrylates of formula (I) can also be protected against unwanted polymerization by the addition of stabilizers. Such stabilizers may be oxygenous gas or else chemical stabilizers, as described, for example, in Houben-Weyl, Methoden der organischen Chemie [Methods of Organic Chemistry], 4th edition, volume XIV/1, Georg Thieme Verlag, Stuttgart 1961, page 433 ff. Examples are: sodium dithionite, sodium hydrogensulphide, sulphur, hydrazine, phenylhydrazine, hydrazobenzene, N-phenyl-β-naphthylamine, N-phenylethanoldiamine, dinitrobenzene, picric acid, p-nitrosodimethylaniline, diphenylnitrosamine, phenols such as para-methoxyphenol, 2,5-di-tert-butylhydroquinone, 2,6-di-tert-butyl-4-methylphenol, p-tert-butylcatechol or 2,5-di-tert-amylhydroquinone, tetramethylthiuram disulphide, 2-mercaptobenzothiazole, sodium dimethyldithiocarbamate, phenothiazine, N-oxyl compounds, for example 2,2,6,6-tetramethylpiperidine N-oxide (TEMPO) or one of its derivatives. Preference is given to 2,6-di-tert-butyl-4-methylphenol and para-methoxyphenol, and mixtures thereof. These stabilizers are typically used in an amount of 0.001% to 1% by weight, preferably 0.01% to 0.5% by weight, based on the phenylurethane acrylate to be stabilized.

Suitable hydroxyalkyl acrylates are 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, 2-hydroxyalkyl acrylate and 2-hydroxyalkyl methacrylate having up to 8 carbon atoms in the alkyl group $R^1$ in formula (I), 4-hydroxybutyl acrylate, 4-hydroxybutyl methacrylate, 5-hydroxyhexyl acrylate, 5-hydroxyhexyl methacrylate, 8-hydroxyoctyl acrylate, 8-hydroxyoctyl methacrylate, 3-hydroxy-2,2-dimethylpropyl (meth)acrylate and mixtures thereof.

Preference is given to 2-hydroxyethyl acrylate, 2-hydroxyethyl methacrylate, 2-hydroxypropyl acrylate, 2-hydroxypropyl methacrylate, 4-hydroxybutyl acrylate and 4-hydroxybutyl methacrylate and mixtures thereof. Particular preference is given to 2-hydroxyethyl acrylate and 2-hydroxypropyl acrylate, and mixtures thereof.

The substituted phenyl isocyanates can be prepared from the corresponding aromatic amines. Standard methods are the phosgenation of the amine in solvent, gas phase phosgenation, reaction with phenoxycarbonyl chloride and subsequent elimination of phenol, reaction with an aromatic diisocyanate and subsequent thermal cleavage and distillative removal of the substituted phenyl isocyanate.

The substituted phenyl isocyanates can then be converted by urethanization with the hydroxyalkyl (meth)acrylates to the inventive compounds of the formula (I).

Suitable substituted phenyl isocyanates are isomeric biphenyl isocyanates, the isomeric phenylthiophenyl isocyanates, the isomeric phenylthiobiphenyl isocyanates, the isomeric phenylthiophenylthiophenyl isocyanates, the isomeric bis(phenylthio)phenyl isocyanates. In addition, the aforementioned substituted phenyl isocyanates may additionally bear an alkyl group having up to 8 carbon atoms and/or an alkylthio group having up to 4 carbon atoms and/or a halogen. Preferred alkyl groups as further substituents are methyl, ethyl, propyl, butyl and hexyl. Preferred alkylthio groups are the methylthio and ethylthio groups. Preferred halogens are fluorine and chlorine. Thus, suitable phenyl isocyanates are, for example, 2-isocyanato-5-methylbiphenyl, 2-isocyanato-5-ethylbiphenyl, 2-isocyanato-5-propylbiphenyl, 2-isocyanato-5-butylbiphenyl, 2-isocyanato-5-hexylbiphenyl, 2-isocyanato-5-octylbiphenyl, 6-isocyanatobiphenyl-3-yl methyl sulphide, 6-isocyanatobiphenyl-3-yl ethyl sulphide, 6-isocyanatobiphenyl-3-yl phenyl sulphide, 2-isocyanato-2'-methylbiphenyl, 2-isocyanato-2'-ethylbiphenyl, 2-isocyanato-2'-propylbiphenyl, 2-isocyanato-2'-butylbiphenyl, 2-fluoro-2'-isocyanatobiphenyl, 2-chloro-2'-isocyanatobiphenyl, 2-bromo-2'-isocyanatobiphenyl, 2-iodo-2'-isocyanatobiphenyl, 2'-isocyanatobiphenyl-2-yl methyl sulphide, 2'-isocyanatobiphenyl-2-yl ethyl sulphide, 2'-isocyanatobiphenyl-2-yl phenyl sulphide, 5-fluoro-2-isocyanatobiphenyl, 5-chloro-2-isocyanatobiphenyl, 5-bromo-2-isocyanatobiphenyl, 5-iodo-2-isocyanatobiphenyl, 2-isocyanato-3,5-dimethylbiphenyl, 2,3,4,5-tetrafluoro-6-isocyanatobiphenyl, 2-isocyanato-5-methylphenyl phenyl sulphide, 2-isocyanato-5-ethylphenyl phenyl sulphide, 2-isocyanato-5-propylphenyl phenyl sulphide, 2-isocyanato-5-butylphenyl phenyl sulphide, 5-fluoro-2-isocyanatophenyl phenyl sulphide, 5-chloro-2-isocyanatophenyl phenyl sulphide, 1-isocyanato-4-(methylsulphanyl)-2-(phenylsulphanyl)benzene, 4-(ethylsulphanyl)-1-isocyanato-2-(phenylsulphanyl)benzene, 2-isocyanato-3,5-dimethylphenyl phenyl sulphide, 1-isocyanate-2-[(2-methylphenyl)sulphanyl]benzene, 1-isocyanate-2-[(2-ethylphenyl)sulphanyl]benzene, 1-isocyanato-2-[(2-propylphenyl)sulphanyl]benzene, 1-isocyanato-2-[(2-butylphenyl)sulphanyl]benzene, 1-isocyanato-2-[(2-hexylphenyl)sulphanyl]benzene, 1-fluoro-2-[(2-isocyanatophenyl)sulphanyl]benzene, 1-chloro-2-[(2-isocyanatophenyl)sulphanyl]benzene, 1-bromo-2-[(2-isocyanatophenyl)sulphanyl]benzene, 1-iodo-2-[(2-isocyanatophenyl)sulphanyl]benzene and regioisomers thereof.

Preferred substituted phenyl isocyanates are biphenyl isocyanate, phenylthiophenyl isocyanate, phenylthiobiphenyl isocyanate, phenylthiophenylthiophenyl isocyanate and bis(phenylthio)phenyl isocyanate.

Particularly preferred substituted phenyl isocyanates are 2-biphenyl isocyanate, 2-phenylthiophenyl isocyanate and 1-isocyanato-2-{[3-(phenylsulphanyl)phenyl]sulphanyl}benzene.

Also suitable are substituted naphthyl isocyanates, for example 1-isocyanato-4-phenylnaphthalene,4-isocyanato-5-methyl-1-phenylnaphthalene, 4-isocyanato-5-ethyl-1-phenylnaphthalene, 4-isocyanato-5-butyl-1-phenylnaphthalene, 5-fluoro-4-isocyanate-1-phenylnaphthalene, 5-chloro-4-isocyanato-1-phenylnaphthalene, 5-bromo-4-isocyanato-1-phenylnaphthalene, 5-iodo-4-isocyanato-1-phenylnaphthalene, 4-isocyanato-5-(methylsulphanyl)-1-phenylnaphthalene, 4-isocyanato-5-(ethylsulphanyl)-1-phenylnaphthalene, 4-isocyanato-1-naphthyl phenyl sulphide, 4-isocyanato-5-methyl-1-naphthyl phenyl sulphide, 4-isocyanato-5-ethyl-1-naphthyl phenyl sulphide, 4-isocyanato-5-propyl-1-naphthyl phenyl sulphide, 4-isocyanato-5-butyl-1-naphthyl phenyl sulphide, 4-isocyanato-5-octyl-1-naphthyl phenyl sulphide, 5-fluoro-4-isocyanato-1-naphthyl phenyl sulphide, 5-chloro-4-isocyanato-1-naphthyl phenyl sulphide, 5-bromo-4-isocyanato-1-naphthyl phenyl sulphide, 5-iodo-4-isocyanato-1-naphthyl phenyl sulphide, 4-isocyanato-5-(methylsulphanyl)-1-(phenylsulphanyl)naphthalene, 4-isocyanato-5-(ethylsulphanyl)-1-(phenylsulphanyl) naphthalene and regioisomers thereof. Preference is given to 1-isocyanato-4-phenylnaphthalene and 4-isocyanato-1-naphthyl phenyl sulphide.

In the compound of the formula (I), the $R^3$ radical may be a phenyl or phenylthiyl radical substituted by one or more phenyl, phenythiyl, alkyl, alkylthiyl, halogen, biphenyl, naphthyl radicals.

According to a preferred embodiment, however, in the compound of the formula (I), the $R^3$ radical is selected from the group of phenyl, phenylthiyl, phenylthiylphenylthiyl.

It is likewise preferable when, in the compound of the formula (I), Ar is a radical of formula (II). It is also especially preferable when, in the compound of the formula (I), Ar is a radical of the formula (II) and, in the compound of the formula (II), n=1.

According to a further preferred embodiment of the invention, $R^1$ may be a radical selected from the group of —$CH_2$—$CH_2$—, —$CH_2$—$CH_2$—$CH_2$—, —$CH_2$—$CHCH_3$—, —$CH_2$—$CH_2$—$CH_2$—$CH_2$—.

It is preferable when the compound of the formula (I) is selected from the group of 2-[(biphenyl-2-ylcarbamoyl)oxy]ethyl acrylate, 2-[(biphenyl-2-ylcarbamoyl)oxy]ethyl methacrylate, 2-[(biphenyl-2-ylcarbamoyl)oxy]propyl acrylate, 2[(biphenyl-2-ylcarbamoyl)oxy]propyl methacrylate, 2-({[2-(phenylsulphanyl)phenyl]carbamoyl}oxy)ethyl acrylate, 2-({[2-(phenylsulphanyl)phenyl]carbamoyl}oxy)ethyl methacrylate, 2-({[2-(phenylsulphanyl)phenyl]carbamoyl} oxy)propyl acrylate, 2-({[2-(phenylsulphanyl)phenyl]carbamoyl}oxy)propyl methacrylate, 2-{[*2-{[3-(phenylsulphanyl)phenyl]sulphanyl}phenyl]carbamoyl]oxy}ethyl acrylate, 2-{[(2-{[3-(phenylsulphanyl)phenyl]sulphanyl}phenyl)carbamoyl]oxy}ethyl methacrylate, 2-{[(2-{[3-(phenylsulphanyl)phenyl]sulphanyl}phenyl)carbamoyl]oxy}propyl acrylate, 2-{[(2-{[3-(phenylsulphanyl)phenyl]sulphanyl}phenyl)carbamoyl]oxy}propyl methacrylate.

It is very especially preferable when the compound of the formula (I) is selected from the group of 2-[(biphenyl-2-ylcarbamoyl)oxy]ethyl acrylate, 2-[(biphenyl-2-ylcarbamoyl)oxy]propyl acrylate, 2-({[2-(phenylsulphanyl)phenyl]carbamoyl}oxy)ethyl acrylate, 2-({[2-(phenylsulphanyl)

phenyl]carbamoyl}oxy)propyl acrylate, 2-{[2-{[3-(phenylsulphanyl)phenyl]sulphanyl}phenyl)carbamoyl] oxy}ethyl acrylate 2-{[(2-{[3-(phenylsulphanyl)phenyl] sulphanyl}phenyl)carbamoyl]oxy}propyl acrylate.

The present invention further provides a photopolymer comprising matrix polymers, writing monomers and photoinitiators, wherein the writing monomers comprise an inventive compound of formula (I).

Matrix polymers used may be amorphous thermoplastics, for example polyacrylates, polymethylmethacrylates or copolymers of methyl methacrylate, methacrylic acid or other alkyl acrylates and alkyl methacrylates, and also acrylic acid, for example polybutyl acrylate, and also polyvinyl acetate and polyvinyl butyrate, the partially hydrolysed derivatives thereof, such as polyvinyl alcohols, and copolymers with ethylenes and/or further (meth)acrylates, gelatins, cellulose esters and cellulose ethers such as methyl cellulose, cellulose acetobutyrate, silicones, for example polydimethylsilicone, polyurethanes, polybutadienes and polyisoprenes, and also polyethylene oxides, epoxy resins, especially aliphatic epoxy resins, polyamides, polycarbonates and the systems cited in U.S. Pat. No. 4,994,347A and therein.

It is particularly preferable, however, when the matrix polymers are polyurethanes.

It is also particularly preferable when the matrix polymers have been crosslinked. It is especially preferably when the matrix polymers have been three-dimensionally crosslinked.

Epoxy resins may be cationically intercrosslinked. In addition, it is also possible to use acids/anhydrides, amines, hydroxyalkyl amides and thiols as crosslinkers.

Silicones can be crosslinked either as one-component systems through condensation in the presence of water (and optionally under Brønsted acid catalysis) or as two-component systems by addition of silicic esters or organotin compounds. Likewise possible is the hydrosilylations in vinyl-silane systems.

Unsaturated compounds, for example acryloyl-functional polymers or unsaturated esters, can be crosslinked with amines or thiols. Cationic vinyl ether polymerization is also possible.

However, it is especially preferable when the matrix polymers are crosslinked matrix polymers, preferably three-dimensionally crosslinked matrix polymers and most preferably are three-dimensionally crosslinked polyurethanes. Polyurethane matrix polymers are obtainable especially by reaction of at least one polyisocyanate component a) with at least one isocyanate-reactive component b).

The polyisocyanate component a) comprises at least one organic compound having at least two NCO groups. These organic compounds may especially be monomeric di- and triisocyanates, polyisocyanates and/or NCO-functional prepolymers. The polyisocyanate component a) may also contain or consist of mixtures of monomeric di- and triisocyanates, polyisocyanates and/or NCO-functional prepolymers.

Monomeric di- and triisocyanates used may be any of the compounds that are well known per se to those skilled in the art, or mixtures thereof. These compounds may have aromatic, araliphatic, aliphatic or cycloaliphatic structures. The monomeric di- and triisocyanates may also comprise minor amounts of monoisocyanates, i.e. organic compounds having one NCO group.

Examples of suitable monomeric di- and triisocyanates are butane 1,4-diisocyanate, pentane 1,5-diisocyanate, hexane 1,6-diisocyanate (hexamethylene diisocyanate, HDI), 2,2,4-trimethylhexamethylene diisocyanate and/or 2,4,4-trimethylhexamethylene diisocyanate (TMDI), isophorone diisocyanate (IPDI), 1,8-diisocyanato-4-(isocyanatomethyl)octane, bis(4,4'-isocyanatocyclohexyl)methane and/or bis(2',4-isocyanatocyclohexyl)methane and/or mixtures thereof having any isomer content, cyclohexane 1,4-diisocyanate, the isomeric bis(isocyanatomethyl)cyclohexanes, 2,4- and/or 2,6-diisocyanato-1-methylcyclohexane (hexahydrotolylene 2,4- and/or 2,6-diisocyanate, $H_6$-TDI), phenylene 1,4-diisocyanate, tolylene 2,4- and/or 2,6-diisocyanate (TDI), naphthylene 1,5-diisocyanate (NDI), diphenylmethane 2,4'- and/or 4,4'-diisocyanate (MDI), 1,3-bis (isocyanatomethyl)benzene (XDI) and/or the analogous 1,4 isomers or any desired mixtures of the aforementioned compounds.

Suitable polyisocyanates are compounds which have urethane, urea, carbodiimide, acylurea, amide, isocyanurate, allophanate, biuret, oxadiazinetrione, uretdione and/or iminooxadiazinedione structures and are obtainable from the aforementioned di- or triisocyanates.

More preferably, the polyisocyanates are oligomerized aliphatic and/or cycloaliphatic di- or triisocyanates, it being possible to use especially the above aliphatic and/or cycloaliphatic di- or triisocyanates.

Very particular preference is given to polyisocyanates having isocyanurate, uretdione and/or iminooxadiazinedione structures, and biurets based on HDI or mixtures thereof.

Suitable prepolymers contain urethane and/or urea groups, and optionally further structures formed through modification of NCO groups as specified above. Prepolymers of this kind are obtainable, for example, by reaction of the abovementioned monomeric di- and triisocyanates and/or polyisocyanates a1) with isocyanate-reactive compounds b1).

Isocyanate-reactive compounds b1) used may be alcohols, amino or mercapto compounds, preferably alcohols. These may especially be polyols. Most preferably, isocyanate-reactive compound b1) used may be polyester polyols, polyether polyols, polycarbonate polyols, poly(meth)acrylate polyols and/or polyurethane polyols.

Suitable polyester polyols are, for example, linear polyester diols or branched polyester polyols, which can be obtained in a known manner by reaction of aliphatic, cycloaliphatic or aromatic di- or polycarboxylic acids or anhydrides thereof with polyhydric alcohols of OH functionality ≥2. Examples of suitable di- or polycarboxylic acids are polybasic carboxylic acids such as succinic acid, adipic acid, suberic acid, sebacic acid, decanedicarboxylic acid, phthalic acid, terephthalic acid, isophthalic acid, tetrahydrophthalic acid or trimellitic acid, and acid anhydrides such as phthalic anhydride, trimellitic anhydride or succinic anhydride, or any desired mixtures thereof. The polyester polyols may also be based on natural raw materials such as castor oil. It is likewise possible that the polyester polyols are based on homo- or copolymers of lactones, which can preferably be obtained by addition of lactones or lactone mixtures, such as butyrolactone, ε-caprolactone and/or methyl-ε-caprolactone onto hydroxy-functional compounds such as polyhydric alcohols of OH functionality ≥2, for example of the hereinbelow mentioned type.

Examples of suitable alcohols are all polyhydric alcohols, for example the $C_2$-$C_{12}$ diols, the isomeric cyclohexanediols, glycerol or any desired mixtures thereof.

Suitable polycarbonate polyols are obtainable in a manner known per se by reaction of organic carbonates or phosgene with diols or diol mixtures.

Suitable organic carbonates are dimethyl, diethyl and diphenyl carbonate.

Suitable diols or mixtures comprise the polyhydric alcohols of OH functionality ≥2 mentioned per se in the context of the polyester segments, preferably butane-1,4-diol, hexane-1,6-diol and/or 3-methylpentanediol. It is also possible to convert polyester polyols to polycarbonate polyols.

Suitable polyether polyols are polyaddition products, optionally of blockwise structure, of cyclic ethers onto OH- or NH-functional starter molecules.

Suitable cyclic ethers are, for example, styrene oxides, ethylene oxide, propylene oxide, tetrahydrofuran, butylene oxide, epichlorohydrin, and any desired mixtures thereof.

Starters used may be the polyhydric alcohols of OH functionality ≥2 mentioned per se in the context of the polyester polyols, and also primary or secondary amines and amino alcohols.

Preferred polyether polyols are those of the aforementioned type based exclusively on propylene oxide, or random or block copolymers based on propylene oxide with further 1-alkylene oxides. Particular preference is given to propylene oxide homopolymers and random or block copolymers containing oxyethylene, oxypropylene and/or oxybutylene units, where the proportion of the oxypropylene units based on the total amount of all the oxyethylene, oxypropylene and oxybutylene units amounts to at least 20% by weight, preferably at least 45% by weight. Oxypropylene and oxybutylene here encompasses all the respective linear and branched $C_3$ and $C_4$ isomers.

Additionally suitable as constituents of the polyol component b1), as polyfunctional, isocyanate-reactive compounds, are also low molecular weight (i.e. with molecular weights≤500 g/triol), short-chain (i.e. containing 2 to 20 carbon atoms), aliphatic, araliphatic or cycloaliphatic di-, tri- or polyfunctional alcohols.

These may, for example, in addition to the abovementioned compounds, be neopentyl glycol, 2-ethyl-2-butylpropanediol, trimethylpentanediol, positionally isomeric diethyloctanediols, cyclohexanediol, 1,4-cyclohexanedimethanol, 1,6-hexanediol, 1,2- and 1,4-cyclohexanediol, hydrogenated bisphenol A, 2,2-bis(4-hydroxycyclohexyl)propane or 2,2-dimethyl-3-hydroxypropionic acid, 2,2-dimethyl-3-hydroxypropyl ester. Examples of suitable triols are trimethylolethane, trimethylolpropane or glycerol. Suitable higher-functionality alcohols are di(trimethylolpropane), pentaerythritol, dipentaerythritol or sorbitol.

It is especially preferable when the polyol component is a difunctional polyether, polyester, or a polyether-polyester block copolyester or a polyether-polyester block copolymer having primary OH functions.

It is likewise possible to use amines as isocyanate-reactive compounds b1). Examples of suitable amines are ethylenediamine, propylenediamine, diaminocyclohexane, 4,4'-dicyclohexylmethanediamine, isophoronediamine (IPDA), difunctional polyamines, for example the Jeffamines®, amine-terminated polymers, especially having number-average molar masses≤10 000 g/mol. Mixtures of the aforementioned amines can likewise be used.

It is likewise possible to use amino alcohols as isocyanate-reactive compounds b1). Examples of suitable amino alcohols are the isomeric aminoethanols, the isomeric aminopropanols, the isomeric aminobutanols and the isomeric aminohexanols, or any desired mixtures thereof.

All the aforementioned isocyanate-reactive compounds b1) can be mixed with one another as desired.

It is also preferable when the isocyanate-reactive compounds b1) have a number-average molar mass of ≥200 and ≤10 000 g/mol, further preferably ≥500 and ≤8000 g/mol and most preferably ≥800 and ≤5000 g/mol. The OH functionality of the polyols is preferably 1.5 to 6.0, more preferably 1.8 to 4.0.

The prepolymers of the polyisocyanate component a) may especially have a residual content of free monomeric di- and triisocyanates of <1% by weight, more preferably <0.5% by weight and most preferably <0.3% by weight.

It is optionally also possible that the polyisocyanate component a) contains, entirely or in part, organic compound whose NCO groups have been fully or partly reacted with blocking agents known from coating technology. Examples of blocking agents are alcohols, lactams, oximes, malonic esters, pyrazoles, and amines, for example butanone oxime, diisopropylamine, diethyl malonate, ethyl acetoacetate, 3,5-dimethylpyrazole, ε-caprolactam, or mixtures thereof.

It is especially preferable when the polyisocyanate component a) comprises compounds having aliphatically bonded NCO groups, aliphatically bonded NCO groups being understood to mean those groups that are bonded to a primary carbon atom. The isocyanate-reactive component b) preferably comprises at least one organic compound having an average of at least 1.5 and preferably 2 to 3 isocyanate-reactive groups. In the context of the present invention, isocyanate-reactive groups are regarded as being preferably hydroxyl, amino or mercapto groups.

The isocyanate-reactive component may especially comprise compounds having a numerical average of at least 1,5 and preferably 2 to 3 isocyanate-reactive groups.

Suitable polyfunctional isocyanate-reactive compounds of component b) are for example the above-described compounds b1).

It is also most preferable when the polyurethanes are based on polyester C4 polyether polyols.

Photoinitiators of the component are compounds activatable typically by means of actinic radiation, which can trigger polymerization of the writing monomers. In the case of the photoinitiators, a distinction can be made between unimolecular (type I) and bimolecular (type II) initiators. In addition, they are distinguished by their chemical nature as photoinitiators for free-radical, anionic, cationic or mixed types of polymerization.

Type I photoinitiators (Norrish type I) for free-radical photopolymerization form free radicals on irradiation through unimolecular bond scission. Examples of type I photoinitiators are triazines, oximes, benzoin ethers, benzil ketals, bisimidazoles, aroylphosphine oxides, sulphonium salts and iodonium salts.

Type II photoinitiators (Norrish type II) for free-radical polymerization consist of a dye as sensitizer and a coinitiator, and undergo a bimolecular reaction on irradiation with light attuned to the dye. First of all, the dye absorbs a photon and transfers energy from an excited state to the coinitiator. The latter releases the polymerization-triggering free radicals through electron or proton transfer or direct hydrogen abstraction.

In the context of this invention, preference is given to using type II photoinitiators.

Photoinitiator systems of this kind are described in principle in EP 0 223 587 A and consist preferably of a mixture of one or more dyes with ammonium alkylarylborate(s).

Suitable dyes which, together with an ammonium alkylarylborate, form a type II photoinitiator are the cationic dyes described in WO 2012062655, in combination with the anions likewise described therein.

Cationic dyes are preferably understood to mean those from the following classes: acridine dyes, xanthene dyes, thioxanthene dyes, phenazine dyes, phenoxazine dyes, phenothiazine dyes, tri(het)arylmethane dyes—especially diamino- and triamino(het)arylmethane dyes, mono-, di-, tri- and pentamethinecyanine dyes, hemicyanine dyes, externally cationic merocyanine dyes, externally cationic neutrocyanine dyes, zeromethine dyes—especially naphtholactam dyes, streptocyanine dyes. Dyes of this kind are described, for example, in H. Berneth in Ullmann's Encyclopedia of Industrial Chemistry, Azine Dyes, Wiley-VCH Verlag, 2008, H. Berneth in Ullmann's Encyclopedia of Industrial Chemistry, Methine Dyes and Pigments, Wiley-VCH Verlag, 2008, T. Gessner, U. Mayer in Ullmann's Encyclopedia of Industrial Chemistry, Triarylmethane and Diarylmethane Dyes, Wiley-VCH Verlag, 2000.

Particular preference is given to phenazine dyes, phenoxazine dyes, phenothiazine dyes, tri(het)arylmethane dyes—especially diamine- and triamino(het)arylmethane dyes, mono-, di-, tri- and pentamethinecyanine dyes, hemicyanine dyes, zeromethine dyes—especially naphtholactam dyes, streptocyanine dyes.

Examples of cationic dyes are Astrazon Orange G, Basic Blue 3, Basic Orange 22, Basic Red 13, Basic Violet 7, Methylene Blue, New Methylene Blue, Azure A, 2,4-diphenyl-6-(4-methoxyphenyl)pyrylium, Safranin O, Astraphloxin, Brilliant Green, Crystal Violet, Ethyl Violet and thionine.

Preferred anions are especially $C_8$- to $C_{23}$-alkanesulphonate, preferably $C_{13}$- to $C_{25}$-alkanesulphonate, $C_3$- to $C_{18}$-perfluoroalkanesulphonate, $C_4$- to $C_{18}$-perfluoroalkanesulphonate bearing at least 3 hydrogen atoms in the alkyl chain, $C_9$- to $C_{25}$-alkanoate, $C_9$- to $C_{25}$-alkenoate, $C_8$- to $C_{25}$-alkylsulphate, preferably $C_{13}$- to $C_{25}$-alkylsulphate, $C_8$- to $C_{25}$-alkenylsulphate, preferably $C_{13}$- to $C_{25}$-alkenylsulphate, $C_3$- to $C_{18}$-perfluoroalkylsulphate, $C_4$- to $C_{18}$-perfluoroalkylsulphate bearing at least 3 hydrogen atoms in the alkyl chain, polyether sulphates based on at least 4 equivalents of ethylene oxide and/or 4 equivalents of propylene oxide, bis($C_4$- to $C_{25}$-alkyl, $C_5$- to $C_7$-cycloalkyl, to $C_8$-alkenyl or $C_7$- to $C_{11}$-aralkyl)sulphosuccinate, bis-$C_2$-to $C_{10}$-alkylsulphosuccinate substituted by at least 8 fluorine atoms, $C_8$- to $C_{25}$-alkylsulphoacetates, benzenesulphonate substituted by at least one radical from the group of halogen, $C_4$- to $C_{25}$-alkyl, perfluoro-$C_1$- to $C_8$-alkyl and/or $C_1$- to $C_{12}$-alkoxycarbonyl, naphthalene- or biphenylsulphonate optionally substituted by nitro, cyano, hydroxyl, $C_1$- to $C_{25}$-alkyl, $C_1$- to $C_{12}$-alkoxy, amino, $C_1$- to $C_{12}$-alkoxycarbonyl or chlorine, benzene-, naphthalene- or biphenyldisulphonate optionally substituted by nitro, cyano, hydroxyl, $C_1$- to $C_{25}$-alkyl, $C_1$- to $C_{12}$-alkoxy, $C_1$- to $C_{12}$-alkoxycarbonyl or chlorine, benzoate substituted by dinitro, $C_6$- to $C_{25}$-alkyl, $C_4$- to $C_{12}$-alkoxycarbonyl, benzoyl, chlorobenzoyl or tolyl, the anion of naplathalenedicarboxylic acid, diphenyl ether disulphonate, sulphonated or sulphated, optionally at least monounsaturated $C_8$ to $C_{25}$ fatty acid esters of aliphatic $C_1$ to $C_8$ alcohols or glycerol, bis(sulpho-$C_2$- to $C_6$-alkyl) $C_3$- to $C_{12}$-alkanedicarboxylates, bis(sulpho-$C_2$- to $C_6$-alkyl) itaconates, (sulpho-$C_2$- to $C_6$-alkyl) $C_6$- to $C_{18}$-alkanecarboxylates, (sulpho-$C_2$- to $C_6$-alkyl) acrylates or methacrylates, triscatechol phosphate optionally substituted by up to 12 halogen radicals, an anion from the group of tetraphenylborate, cyanotriphenylborate, tetraphenoxyborate, $C_4$- to $C_{12}$-alkyltriphenylborate wherein the phenyl or phenoxy radicals may be substituted by halogen, $C_1$- to $C_4$-alkyl and/or $C_1$- to $C_4$-alkoxy, $C_4$- to $C_{12}$-alkyltrinaphthylborate, tetra-$C_1$- to $C_{20}$-alkoxyborate, 7,8- or 7,9-dicarba-nido-undecaborate(1-) or (2-), which are optionally substituted on the boron and/or carbon atoms by one or two $C_1$- to $C_{12}$-alkyl or phenyl groups, dodecahydrodicarbadodecaborate(2-) or B—$C_1$- to $C_{12}$-alkyl-C-phenyldodecahydrodicarbadodecaborate(1-), where, in the case of polyvalent anions such as naphthalenedisulphonate, $A^-$ represents one equivalent of this anion, and where the alkane and alkyl groups may be branched and/or may be substituted by halogen, cyano, methoxy, ethoxy, methoxycarbonyl or ethoxycarbonyl.

It is also preferable when the anion $A^-$ of the dye has an AClogP in the range from 1 to 30, more preferably in the range from 1 to 12 and especially preferably in the range from 1 to 6.5. AClogP is calculated according to J. Comput. Aid. Mol. Des. 2005, 19, 453; Virtual Computational Chemistry Laboratory, http://www.vcclab.org.

Suitable ammonium alkylarylborates are, for example (Cunningham et al., RadTech'98 North America UV/EB Conference Proceedings, Chicago, Apr. 19-22, 1998): tetrabutylammonium triphenylhexylborate, tetrabutylammonium triphenylbutylborate, tetrabutylammonium trinaphthylhexylborate, tetrabutylammonium tris(4-tert-butyl)phenylbutylborate, tetrabutylammonium tris(3-fluorophenyl)hexylborate hexylborate ([191726-69-9], CGI 7460, product from BASF SE, Basle, Switzerland), 1-methyl-3-octylimidazolium dipentyldiphenylborate and tetrabutylammonium tris (3-chloro-4-methylphenyl)hexylborate ([1147315-11-4], CGI 909, product from BASF SE, Basle, Switzerland).

It may be advantageous to use mixtures of these photoinitiators. According to the radiation source used, the type and concentration of photoinitiator has to be adjusted in the manner known to those skilled in the art. Further details are described, for example, in P. K. T. Oldring (Ed.), Chemistry & Technology of UV & EB Formulations For Coatings, Inks & Paints, Vol. 3, 1991, SITA Technology, London, p. 61-328.

It is most preferable when the photoinitiator comprises a combination of dyes whose absorption spectra at least partly cover the spectral range from 400 to 800 nm, with at least one coinitiator matched to the dyes.

It is also preferable when at least one photoinitiator suitable for a laser light colour selected from blue, green and red is present in the photopolymer formulation.

It is also further preferable when the photopolymer formulation contains one suitable photoinitiator each for at least two laser light colours selected from blue, green and red.

Finally, it is most preferable when the photopolymer formulation contains one suitable photoinitiator for each of the laser light colours blue, green and red.

Particularly high refractive index contrasts can be achieved when the photopolymer formulation comprises, as further writing monomer, as well as the compound of the formula (I), an acrylate- or methacrylate-functional writing monomer. Particular preference is given to monofunctional writing monomers and especially to those monofunctional urethane (meth)acrylates described in US 2010/0036013 A1.

Suitable acrylate writing monomers are especially compounds of the general formula (IV)

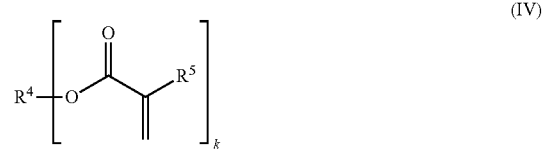

in which k≥1 and k≤4 and $R^4$ is a linear, branched, cyclic or heterocyclic unsubstituted or else optionally heteroatom-substituted organic moiety and/or $R^5$ is hydrogen, a linear, branched, cyclic or heterocyclic unsubstituted or else optionally heteroatom-substituted organic moiety. More preferably, $R^5$ is hydrogen or methyl and/or $R^4$ is a linear, branched, cyclic or heterocyclic organic moiety which is unsubstituted or else optionally substituted with heteroatoms.

Acrylates and methacrylates refer, respectively, to esters of acrylic acid and methacrylic acid. Examples of acrylates and methacrylates usable with preference are phenyl acrylate, phenyl methacrylate, phenoxyethyl acrylate, phenoxyethyl methacrylate, phenoxyethoxyethyl acrylate, phenoxyethoxyethyl methacrylate, phenylthioethyl acrylate, phenylthioethyl methacrylate, 2-naphthyl acrylate, 2-naphthyl methacrylate, 1,4-bis(2-thionaphthyl)-2-butyl acrylate, 1,4-bis(2-thionaphthyl)-2-butyl methacrylate, bisphenol A diacrylate, bisphenol A dimethacrylate, and the ethoxylated analogue compounds thereof, N-carbazolyl acrylates.

Urethane acrylates are understood to mean compounds having at least one acrylic ester group and at least one urethane bond. Compounds of this kind can be obtained, for example, by reacting a hydroxy-functional acrylate or methacrylate with an isocyanate-functional compound.

Examples of isocyanate-functional compounds usable for this purpose are monoisocyanates, and the monomeric diisocyanates, triisocyanates and/or polyisocyanates mentioned under a). Examples of suitable monoisocyanates are phenyl isocyanate, the isomeric methylthiophenyl isocyanates. Di-, tri- or polyisocyanates have been mentioned above, and also triphenylmethane 4,4',4"-triisocyanate and tris(p-isocyanatophenyl) thiophosphate or derivatives thereof with urethane, urea, carbodimide, acylurea, isocyanurate, allophanate, biuret, oxadiazinetrione, uretdione, iminooxadiazinedione structure and mixtures thereof. Preference is given to aromatic di-, tri- or polyisocyanates.

Useful hydroxy-functional acrylates or methacrylates for the preparation of urethane acrylates include, for example, compounds such as 2-hydroxyethyl (meth)acrylate, polyethylene oxide mono(meth)acrylates, polypropylene oxide mono(meth)acrylates, polyalkylene oxide mono(meth)acrylates, poly(ε-caprolactone) mono(meth)acrylates, for example Tone® M100 (Dow, Schwalbach, Del.), 2-hydroxypropyl (meth)acrylate, 4-hydroxybutyl (meth)acrylate, 3-hydroxy-2,2-dimethylpropyl (meth)acrylate, hydroxypropyl (meth)acrylate, 2-hydroxy-3-phenoxypropyl acrylate, the hydroxy-functional mono-, di- or tetraacrylates of polyhydric alcohols such as trimethylolpropane, glycerol, pentaerythritol, dipentaerythritol, ethoxylated, propoxylated or alkoxylated trimethylolpropane, glycerol, pentaerythritol, dipentaerythritol or the technical mixtures thereof. Preference is given to 2-hydroxyethyl acrylate, hydroxypropyl acrylate, 4-hydroxybutyl acrylate and poly(ε-caprolactone) mono(meth)acrylate.

It is likewise possible to use the fundamentally known hydroxyl-containing epoxy (meth)acrylates having OH contents of 20 to 300 mg KOH/g or hydroxyl-containing polyurethane (meth)acrylates having OH contents of 20 to 300 mg KOH/g or acrylated polyacrylates having OH contents of 20 to 300 mg KOH/g and mixtures thereof, and mixtures with hydroxyl-containing unsaturated polyesters and mixtures with polyester (meth)acrylates or mixtures of hydroxyl-containing unsaturated polyesters with polyester (meth)acrylates.

Preference is given especially to urethane acrylates obtainable from the reaction of tris(p-isocyanatophenyl) thiophosphate and/or m-methylthiophenyl isocyanate with alcohol-functional acrylates such as hydroxyethyl (meth)acrylate, hydroxypropyl (meth)acrylate and/or hydroxybutyl (meth)acrylate.

It is likewise possible that the writing monomer comprises or consists of further unsaturated compounds such as α,β-unsaturated carboxylic acid derivatives, for example maleates, fumarates, maleimides, acrylamides, and also vinyl ethers, propenyl ethers, allyl ethers and compounds containing dicyclopentadienyl units, and also olefinically unsaturated compounds, for example styrene, α-methylstyrene, vinyltoluene and/or olefins.

In a further preferred embodiment, the photopolymer additionally comprises monomeric fluorourethanes.

It is particularly preferable when the fluorourethanes comprise or consist of at least one compound of the formula (V)

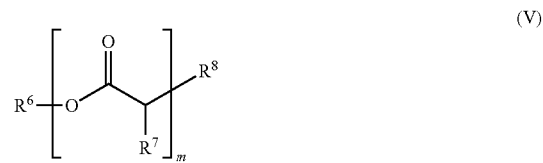

in which m≥1 and m≤8 and $R^6$, $R^7$, $R^8$ are each independently hydrogen or linear, branched, cyclic or heterocyclic organic radicals which are unsubstituted or else optionally substituted by heteroatoms, where preferably at least one of the $R^6$, $R^7$, $R^8$ radicals is substituted by at least one fluorine atom and, more preferably, $R^6$ is an organic radical having at least one fluorine atom.

It a further preferred embodiment of the invention, the photopolymer comprises 10% to 89.999% by weight, preferably 20% to 70% by weight, of matrix polymers, 3% to 60% by weight, preferably 10% to 50% by weight, of writing monomers, 0.001% to 5% by weight, preferably 0.5% to 3% by weight, of photoinitiators and optionally 0% to 4% by weight, preferably 0% to 2% by weight, of catalysts, 0% to 5% by weight, preferably 0.001% to 1% by weight, of stabilizers, 0% to 40% by weight, preferably 10% to 30% by weight, of monomeric fluorourethanes and 0% to 5% by weight, preferably 0.1% to 5% by weight, of further additives, where the sum total of all the constituents is 100% by weight.

Particular preference is given to using photopolymers comprising 20% to 70% by weight of matrix polymers, 20% to 50% by weight of writing monomers, 0.001% to 5% by weight of photoinitiators, 0% to 2% by weight of catalysts, 0.001% to 1% by weight of free-radical stabilizers, optionally 10% to 30% by weight of fluorourethanes and optionally 0.1% to 5% by weight of further additives.

Catalysts used may be urethanization catalysts, for example organic or inorganic derivatives of bismuth, of tin, of zinc or of iron (see also the compounds specified in US 2012/062658), Particularly preferred catalysts are butyltin tris(2-ethylhexanoate), iron(III) trisacetylacetonate, bismuth (III) tris(2-ethylhexanoate) and tin(II) bis(2-ethylhexanoate). In addition, it is also possible to use sterically hindered amines as catalysts.

Stabilizers used may be free-radical inhibitors such as HALS amines, N-alkyl HALS, N-alkoxy HALS and N-alkoxyethyl HALS compounds, and also antioxidants and/or UV absorbers.

Further additives used may be levelling assistants and/or antistats and/or thixotropic agents and/or thickeners and/or biocides.

The invention further provides a holographic medium comprising or consisting of the inventive photopolymer.

The holographic medium may be in particular a film, preferably with a film thickness of 0.3 µm to 500 µm, more preferably with a film thickness of 0.5 µm to 200 µm and yet more preferably with a film thickness of 1 µm to 100 µm.

In one preferred embodiment of the holographic medium according to the present invention, a hologram has been exposed into same, More particularly, the hologram may be a reflection, transmission, in-line, off-axis, full-aperture transfer, white light transmission, Denisyuk, off-axis reflection or edge-lit hologram, or else a holographic stereogram, and preferably a reflection, transmission or edge-lit hologram.

Possible optical functions of the holograms correspond to the optical functions of light elements such as lenses, mirrors, deflecting mirrors, filters, diffuser lenses, directed diffusion elements, diffraction elements, light guides, waveguides, projection lenses and/or masks. In addition, a plurality of such optical functions can be combined in such a hologram, for example such that the light is deflected in a different direction according to the incidence of light. For example, it is possible with such setups to build autostereoscopic or holographic electronic displays which allow a stereoscopic visual impression to be experienced without further aids, for example polarizer or shutter glasses, of the use in automobile head-up displays or head-mounted displays.

These optical elements frequently have a specific frequency selectivity according to how the holograms have been exposed and the dimensions of the hologram. This is important especially when monochromatic light sources such as LEDs or laser light are used. For instance, one hologram is required per complementary colour (RGB), in order to deflect light in a frequency-selective manner and at the same time to enable full-colour displays. Therefore, in particular display setups, several holograms have to be exposed in the medium in a superposed manner.

In addition, by means of the media of the present invention, it is also possible to produce holographic images or representations, for example for personal portraits, biometric representations in security documents, or generally of images or image structures for advertising, security labels, brand protection, branding, labels, design elements, decorations, illustrations, collectable cards, images and the like, and also images which can represent digital data, including in combination with the products detailed above. Holographic images can have the impression of a three-dimensional image, but they may also represent image sequences, short films or a number of different objects according to the angle from which and the light source with which (including moving light sources) etc. they are illuminated. Because of this variety of possible designs, holograms, especially volume holograms, constitute an attractive technical solution for the abovementioned application. It is also possible to use such holograms for storage of digital data, using a wide variety of different exposure methods (shift, spatial or angular multiplexing).

The present invention also provides a process for producing a holographic medium by using a photopolymer formulation of the present invention.

Thus, the photopolymers can especially be used for production of holographic media in the form of a film. In this case, a ply of a material or material composite transparent to light within the visible spectral range (transmission greater than 85% within the wavelength range from 400 to 780 nm) as carrier substrate is coated on one or both sides, and a cover layer is optionally applied to the photopolymer ply or plies.

Preferred materials or material composites for the carrier substrate are based on polycarbonate (PC), polyethylene terephthalate (PET), polybutylene terephthalate, polyethylene, polypropylene, cellulose acetate, cellulose hydrate, cellulose nitrate, cycloolefin polymers, polystyrene, polyepoxides, polysulphone, cellulose triacetate (CTA), polyamide (PA), polymethylmethacrylate (PMMA), polyvinyl chloride, polyvinylbutyral or polydicyclopentadiene or mixtures thereof. They are more preferably based on PC, PET, PA, PMMA and CTA. Material composites may be film laminates or coextrudates. Preferred material composites are duplex and triplex films formed according to one of the schemes A/B, A/B/A or A/B/C. Particular preference is given to PC/PET, PET/PC/PET and PC/TPU (TPU=thermoplastic polyurethane).

The materials or material composites of the carrier substrate may be given an antiadhesive, antistatic, hydrophobized or hydrophilized finish on one or both sides. The modifications mentioned serve the purpose, on the side facing the photopolymer layer, of making the photopolymer ply detachable without destruction from the carrier substrate. Modification of the opposite side of the carrier substrate from the photopolymer ply serves to ensure that the inventive media satisfy specific mechanical demands which exist, for example, in the case of processing in roll laminators, especially in roll-to-roll processes.

The invention likewise provides an optical display comprising an inventive holographic medium.

Examples of such optical displays are imaging displays based on liquid crystals, organic light-emitting diodes (OLEDs), LED display panels, microelectromechanical systems (MEMS) based on diffractive tight selection, electrowetting displays (E-ink) and plasma display screens. Optical displays of this kind may be autostereoscopic and/or holographic displays, transmittive and reflective projection screens, displays with switchable restricted emission characteristics for privacy filters and bidirectional multiuser screens, virtual displays, head-up displays, head-mounted displays, illumination symbols, warning lamps, signal lamps, floodlights and display panels.

The invention likewise provides autostereoscopic and/or holographic displays, projection screens, displays with switchable restricted emission characteristics for privacy filters and bidirectional multiuser screens, virtual displays, head-up displays, head-mounted displays, illumination symbols, warning lamps, signal lamps, floodlights and display panels, comprising an inventive holographic medium.

The invention still further provides a security document and a holographic optical element comprising an inventive holographic medium.

In addition, the invention also provides for the use of an inventive holographic medium for production of chip cards, identity documents, 3D images, product protection labels, labels, banknotes or holographic optical elements, especially for visual displays.

The invention further provides for the use of the compound of the formula (I) as writing monomer in photopolymers, holographic media and/or holographic optical elements.

ExampleS

The invention will now be more particularly elucidated by means of examples.

Figure 2:
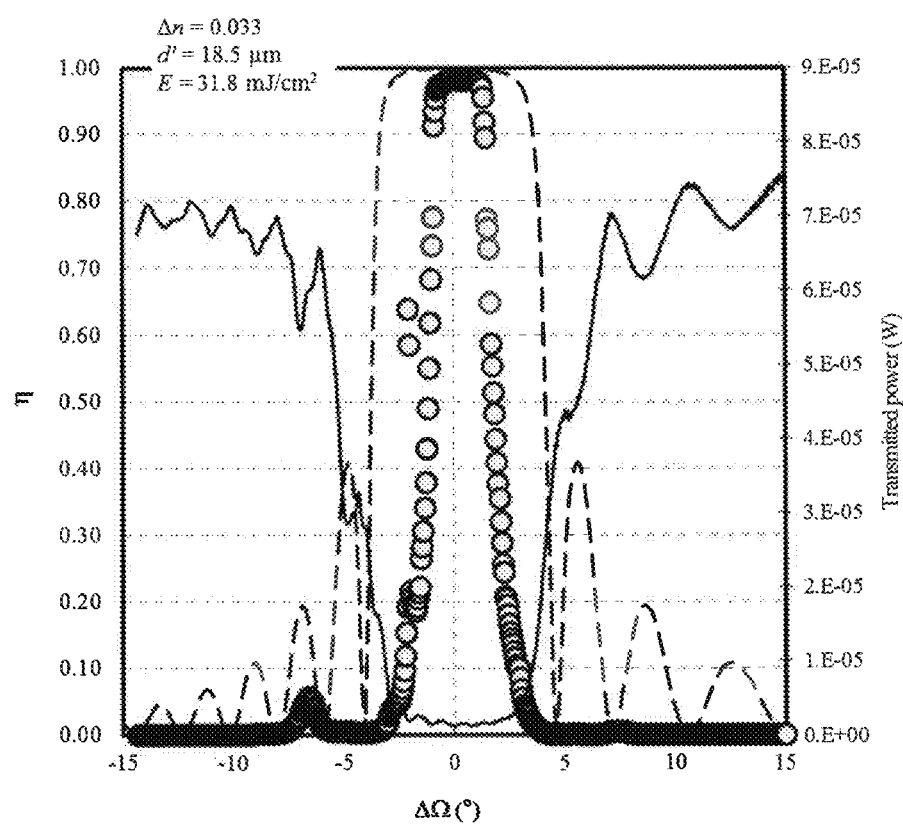

The drawings show:

FIG. 1 the geometry of a holographic media tester (HMT) at λ=532 nm (DPSS laser=diode pumped solid state laser), FIG. 2 the measured diffraction efficiency η as circles plotted against the angle detuning ΔΩ and the fit to the Kogelnik theory as a solid line. The figure shows Example 2.

Figure 3:
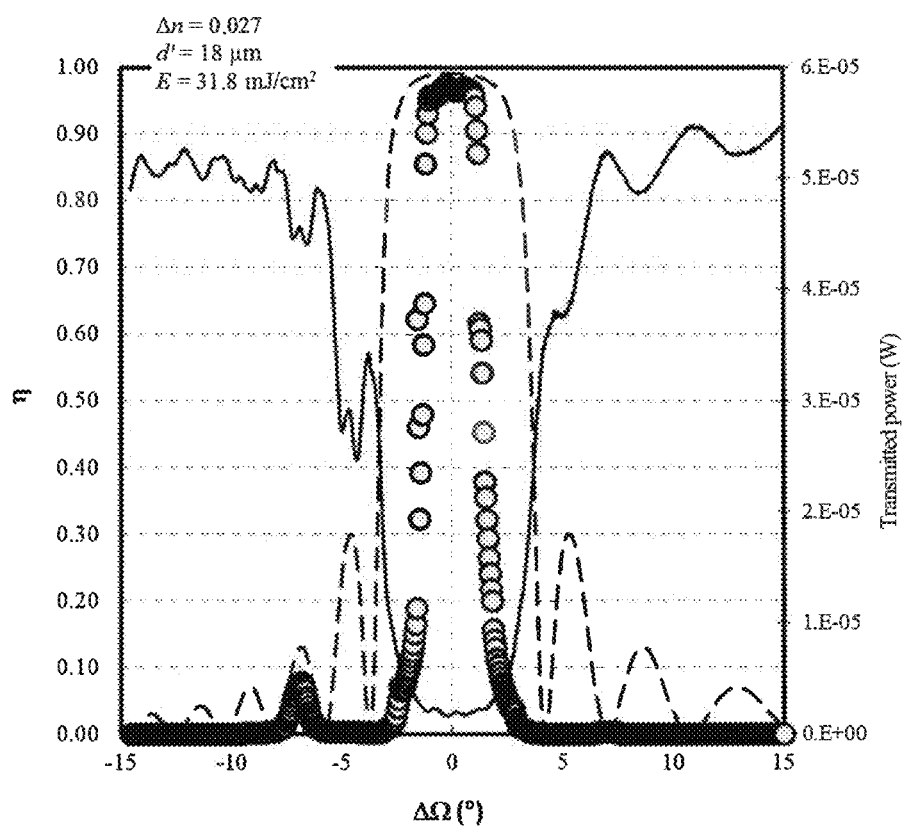

FIG. 3 the measured diffraction efficiency η as circles plotted against the angle detuning ΔΩ and the fit to the Kogelnik theory as a solid line. The figure shows Example 4.

Figure 4:
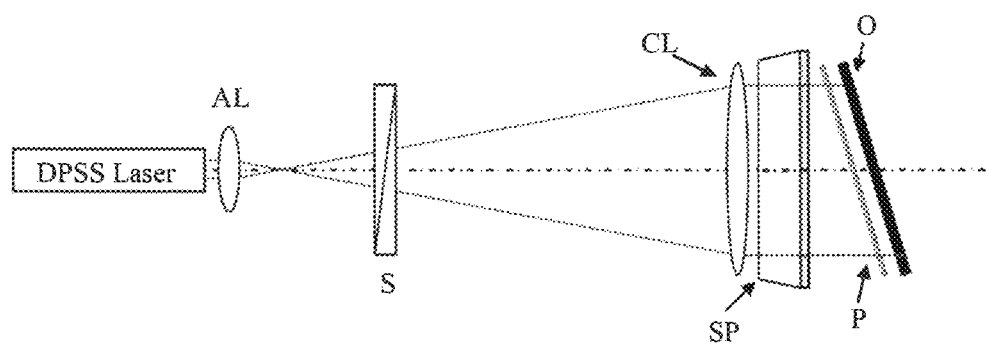

FIG. 4 a setup for writing of Denisyuk holograms.

METHODS OF MEASUREMENT

Determination of Viscosity:

Viscosity was determined with a Physica MCR 51 (from Anton Paar) viscometer. For this purpose, the sample was equilibrated and a ball was suspended (for low viscosities η<10 000 mPas: 23° C., ball diameter 25 mm (CP-25) and for high viscosities η>10 000 mPas: 50° C., ball diameter 60 mm (CP-60)). About 0.5-1 g of product was placed onto the plate, and the ball was allowed to drop down, such that the ball was fully wetted with product. Excess product was wiped off. The shear rate (about 500 l/s at lower viscosities and about 100 l/s at higher viscosities) was set automatically by the instrument. 20 measurements were made in each case and the mean was determined.

Isocyanate Content

Reported NCO values (isocyanate contents) were quantified to DIN EN ISO 11909.

The full conversion of NCO groups, i.e. the absence thereof, in a reaction mixture was detected by IR spectroscopy. Thus, complete conversion was assumed when no NCO band (2261 cm$^{-1}$) was visible in the IR spectrum of the reaction mixture.

Measurement of the Holographic Properties of Diffraction Efficiency DE and Refractive Index Contrast Δn of the Holographic Media by Means of Twin-Beam Interference in a Reflection Arrangement.

A holographic test setup as shown in FIG. 1 was used to measure the diffraction efficiency (DE) of the media. The beam of a DPSS laser (emission wavelength 532 nm) was converted to a parallel homogeneous beam with the aid of the spatial filter (SF) and together with the collimation lens (CL). The final cross sections of the signal and reference beam are fixed by the iris diaphragms (I). The diameter of the iris diaphragm opening is 0.4 cm. The polarization-dependent beam splitters (PBS) split the laser beam into two coherent beams of identical polarization. By means of the λ/2 plates, the power of the reference beam was set to 0.87 mW and the power of the signal beam to 1.13 mW. The powers were determined using the semiconductor detectors (D) with the sample removed. The angle of incidence ($\alpha_0$) of the reference beam is −21.8°; the angle of incidence ($\beta_0$) of the signal beam is 41.8°. The angles are measured proceeding from the sample normal to the beam direction. According to FIG. 1, therefore, $\alpha_0$ has a negative sign and $\beta_0$ a positive sign. At the location of the sample (medium), the interference field of the two overlapping beams produced a pattern of light and dark strips perpendicular to the angle bisectors of the two beams incident on the sample (reflection hologram). The strip spacing Λ, also called grating period, in the medium is ~225 nm (the refractive index of the medium assumed to be ~1.504).

FIG. 1 shows the geometry of a holographic media tester (HMT) at λ=532 nm (DPSS laser): M=mirror, S=shutter, SF=spatial filter, CL=collimator lens, λ/2=λ/2 plate, PBS=polarization-sensitive beam splitter, D=detector, I=iris diaphragm, $\alpha_0$=−21.8°, $\beta_0$=41.8° are the angles of incidence of the coherent beams measured outside the sample (outside the medium). RD=reference direction of turntable.

Holograms were recorded in the medium in the following manner:

Both shutters (S) are opened for the exposure time t.

Thereafter, with the shutters (S) closed, the medium is allowed 5 minutes for the diffusion of the as yet unpolymerized writing monomers.

The written holograms were then read out in the following manner: The shutter of the signal beam remained closed. The shutter of the reference beam was opened. The iris diaphragm of the reference beam was closed to a diameter of <1 mm. This ensured that the beam was always completely within the previously recorded hologram for all angles of rotation (Ω) of the medium. The turntable, under computer control, swept over the angle range from $\Omega_{min}$ to $\Omega_{max}$ with an angle step width of 0.05°. Ω is measured from the sample normal to the reference direction of the turntable. The reference direction of the turntable is obtained when the angles of incidence of the reference beam and of the signal beam have the same absolute value on recording of the hologram, i.e. $\alpha_0$=−31.8° and $\beta_0$=31.8°. In that case, $\Omega_{recording}$=0°. When $\alpha_0$=−21.8° and $\beta_0$=41.8°, $\Omega_{recording}$ is therefore 10°. In general, for the interference field in the course of recording of the hologram:

$$\alpha_0 = \theta_0 + \Omega_{recording}.$$

$\theta_0$ is the semiangle in the laboratory system outside the medium and, in the course of recording of the hologram:

$$\theta_0 = \frac{\alpha_0 - \beta_0}{2}.$$

Thus, in this case, $\theta_0$=−31.8°. At each setting for the angle of rotation Ω, the powers of the beam transmitted in the zeroth order were measured by means of the corresponding detector D, and the powers of the beam diffracted in the first order by means of the detector D. The diffraction efficiency was calculated at each setting of angle Ω as the quotient of:

$$\eta = \frac{P_D}{P_D + P_T}$$

$P_D$ is the power in the detector for the diffracted beam and $P_T$ is the power in the detector for the transmitted beam.

By means of the process described above, the Bragg curve, which describes the diffraction efficiency η as a function of the angle of rotation Ω, for the recorded hologram, was measured and saved on a computer. In addition, the intensity transmitted into the zeroth order was also recorded against the angle of rotation Ω and saved on a computer.

The maximum diffraction efficiency (DE=$\eta_{max}$) of the hologram, i.e. the peak value thereof, was determined at $\Omega_{reconstruction}$. In some cases, it was necessary for this purpose to change the position of the detector for the diffracted beam in order to determine this maximum value.

The refractive index contrast Δn and the thickness d of the photopolymer layer were now determined by means of coupled wave theory (see: H. Kogelnik, The Bell System Technical Journal, Volume 48, November 1969, Number 9 page 2909-page 2947) from the measured Bragg curve and the angle profile of the transmitted intensity. In this context, it should be noted that, because of the shrinkage in thickness which occurs as a result of the photopolymerization, the strip spacing Λ' of the hologram and the orientation of the strips (slant) can differ from the strip spacing $\Lambda$ of the interference pattern and the orientation thereof. Accordingly, the angle $\alpha_0'$ and the corresponding angle of the turntable $\Omega_{reconstruction}$ at which maximum diffraction efficiency is achieved will also differ from $\alpha_0$ and from the corresponding $\Omega_{recording}$. This alters the Bragg condition. This alteration is taken into account in the evaluation process. The evaluation process is described hereinafter:

All geometric parameters which relate to the recorded hologram and not to the interference pattern are shown as parameters with primes.

For the Bragg curve $\eta(\Omega)$ of a reflection hologram, according to Kogelnik:

$$\eta = \begin{cases} \dfrac{1}{1 - \dfrac{1-(\xi/\nu)^2}{\sin^2\left(\sqrt{\xi^2-\nu^2}\right)}}, & \text{for } \nu^2 - \xi^2 < 0 \\ \dfrac{1}{1 + \dfrac{1-(\xi/\nu)^2}{\sinh^2\left(\sqrt{\nu^2-\xi^2}\right)}}, & \text{for } \nu^2 - \xi^2 \geq 0 \end{cases}$$

with:

$$\nu = \frac{\pi \cdot \Delta n \cdot d'}{\lambda \cdot \sqrt{|c_s \cdot c_r|}}$$

$$\xi = -\frac{d'}{2 \cdot c_s} \cdot DP$$

$$c_s = \cos(\vartheta') - \cos(\psi') \cdot \frac{\lambda}{n \cdot \Lambda'}$$

$$c_r = \cos(\vartheta')$$

$$DP = \frac{\pi}{\Lambda'} \cdot \left(2 \cdot \cos(\psi' - \vartheta') - \frac{\lambda}{n \cdot \Lambda'}\right)$$

$$\psi' = \frac{\beta' + \alpha'}{2}$$

$$\Lambda' = \frac{\lambda}{2 \cdot n \cdot \cos(\psi' - \alpha')}$$

The following holds for the reading out ("reconstruction") of the hologram similarly to the above explanation:

$$\vartheta'_0 = \theta_0 + \Omega$$

$$\sin(\vartheta'_0) = n \cdot \sin(\vartheta')$$

Under the Bragg condition, the "dephasing" DP=0. And it follows correspondingly that:

$$\alpha'_0 = \theta_0 + \Omega_{reconstruction}$$

$$\sin(\alpha'_0) = n \cdot \sin(\alpha')$$

The as yet unknown angle $\beta'$ can be determined from the comparison of the Bragg condition of the interference field in the course of recording of the hologram and the Bragg condition in the course of reconstruction of the hologram, assuming that only shrinkage in thickness takes place. It then follows that:

$$\sin(\beta') = \frac{1}{n} \cdot [\sin(\alpha_0) + \sin(\beta_0) - \sin(\theta_0 + \Omega_{reconstruction})]$$

$\nu$ is the grating intensity, $\xi$ is the detuning parameter and $\psi'$ is the orientation (slant) of the refractive index grating written. $\alpha'$ and $\beta'$ correspond to the angles $\alpha_0$ and $\beta_0$ of the interference field during the recording of the hologram, but measured in the medium and valid for the grating of the hologram (shrinkage in thickness). n is the average refractive index of the photopolymer and was set equal to 1.504. $\lambda$ is the wavelength of the laser light in a vacuum.

The maximum diffraction efficiency (DE=$\eta_{max}$), when $\xi=0$, is then calculated to be:

$$DE = \tanh^2(\nu) = \tanh^2\left(\frac{\pi \cdot \Delta n \cdot d'}{\lambda \cdot \sqrt{\cos(\alpha') \cdot \cos(\alpha' - 2\psi')}}\right)$$

FIGS. 2 and 3 show the measured transmitted power $P_T$ (right-hand y-axis) plotted as a lit solid line against the angle detuning $\Delta\Omega$; the measured diffraction efficiency $\eta$ (left-hand y-axis) is plotted as filled circles against the angle detuning $\Delta\Omega$ (to the extent allowed by the finite size of the detector), and the fitting to the Kogelnik theory as a broken line (left-hand y-axis).

The measured data for the diffraction efficiency, the theoretical Bragg curve and the transmitted intensity are, as shown in FIGS. 2 and 3, plotted against the centred angle of rotation $\Delta\Omega = \Omega_{reconstruction} - \Omega = \alpha'_0 - \vartheta'_0$, also called angle detuning.

Since DE is known, the shape of the theoretical Bragg curve, according to Kogelnik, is determined only by the thickness d' of the photopolymer layer. $\Delta n$ is corrected via DE for a given thickness d' such that measurement and theory for DE are always in agreement. d' is then adjusted until the angle positions of the first secondary minima of the theoretical Bragg curve correspond to the angle positions of the first secondary maxima of the transmitted intensity, and there is additionally agreement in the full width at half maximum (FWHM) for the theoretical Bragg curve and for the transmitted intensity.

Since the direction in which a reflection hologram also rotates when reconstructed by means of an $\Omega$ scan, but the detector for the diffracted light can cover only a finite angle range, the Bragg curve of broad holograms (small d') is not fully covered in an $\Omega$ scan, but rather only the central region, given suitable detector positioning. Therefore, the shape of the transmitted intensity, which is complementary to the Bragg curve, is additionally employed for adjustment of the layer thickness d'.

FIGS. 2 and 3 show the plot of the Bragg curve $\eta$ according to the coupled wave theory (broken line), the measured diffraction efficiency (filled circles) and the transmitted power (black solid line) against the angle detuning $\Delta\Omega$.

For a formulation, this procedure was repeated, possibly several times, for different exposure times t on different media, in order to find the mean energy dose of the incident laser beam in the course of recording of the hologram at which DE reaches the saturation value. The mean energy dose E is calculated as follows from the powers of the two component beams assigned to the angles $\alpha_0$ and $\beta_0$ (reference beam where $P_r$=0.87 mW and signal beam where $P_s$=1.13 mW), the exposure time t and the diameter of the iris diaphragm (0.4 cm):

$$E(\text{mJ/cm}^2) = \frac{2 \cdot [P_r + P_s] \cdot t(s)}{\pi \cdot 0.4^2 \text{ cm}}$$

The powers of the component beams were adjusted such that the same power density is attained in the medium at the angles $\alpha_0$ and $\beta_0$ used.

Chemicals:

In each case, the CAS number, if known, is stated in square brackets.

| | |
|---|---|
| 2-Hydroxyethyl acrylate | [818-61-1] - Sigma-Aldrich Chemie GmbH Steinheim, Germany |
| Hydroxypropyl acrylate | [25584-83-2] - BASF SE, Ludwigshafen Germany |
| 2,6-Di-tert-butyl-4-methylphenol | [128-37-0] - Merck KGaA, Darmstadt, Germany |
| 2-Aminobiphenyl | [90-41-5] - Sigma-Aldrich Chemie GmbH Steinheim, Germany |
| 2-Aminobiphenyl phenyl sulphide | [1134-94-7] - Sigma-Aldrich Chemie GmbH Steinheim, Germany |
| 3-(Methylthio)phenyl isocyanate | [28479-19-8] - Sigma-Aldrich Chemie GmbH Steinheim, Germany |
| 1-Isocyanato-3-(methylsulphanyl)benzene | [28479-19-8] - Sigma-Aldrich Chemie GmbH, Steinheim, Germany |
| Desmodur ® RFE | Tris(p-isocyanatophenyl) thiophosphate, 27% in ethyl acetate, product from Bayer MaterialScience AG, Leverkusen, Germany |
| Dibutyltin dilaurate | [77-58-7] - Sigma-Aldrich Chemie GmbH Steinheim, Germany |
| Fomrez ® UL 28 | Momentive Performance Chemicals, Wilton, CT, USA. |
| Borchi ® Kat 22 | [85203-81-2] - OMG Borchers GmbH, Langenfeld, Germany. |
| BYK-310 | BYK-Chemie GmbH, Wesel, Germany |
| Phenyl chloroformate | [1885-14-9] - Acros Organics, Geel, Belgium |
| Desmodur ® N 3900 | Bayer MaterialScience AG, Leverkusen, DE, hexane diisocyanate-based polyisocyanate, proportion of iminooxadiazinedione at least 30%, NCO content: 23.5%. |
| Desmodur 2460M | Bayer MaterialScience AG, Leverkusen, DE, bis(isocyanatophenyl)methane (MDI)-based isocyanate |
| Desmorapid ® SO | [301-10-0] - Rhein Chemie Rheinau GmbH, Mannheim, Germany |
| CGI-909 | tetrabutylaminonium tris(3-chloro-4-methylphenyl)(hexyl)borate [1147315-11-4], BASF SE |
| Trimethylhexamethylene diisocyanate | [28679-16-5] - ABCR GmbH & Co KG, Karlsruhe, Germany |
| 1H, 1H-7H-Perfluoroheptan-1-ol | [335-99-9] - ABCR GmbH & Co KG, Karlsruhe, Germany |
| Astrazon Rosa FG 200% | [3648-36-0] - DyStar Colours Deutschland GmbH, Frankfurt am Main, Germany |
| Sodium bis(2-ethylhexyl)sulphosuccinate | [45297-26-5] Sigma-Aldrich Chemie GmbH, Steinheim, Germany |

Preparation of 2-phenylthiophenyl isocyanate

In a three-neck flask with precision glass stirrer, under nitrogen, 720 g of 2-aminobiphenyl phenyl sulphide were dissolved in 4.2 kg of toluene and 519 g of potassium carbonate were added while stirring, and the mixture was equilibrated to 10° C. Then 560 g of phenyl chloroformate were added dropwise. The product was filtered off and dried under reduced pressure. This gave 1.15 kg of phenyl [2-(phenylsulphanyl)phenyl]carbamate in the form of a crystalline precipitate.

950 g of phenyl [2-(phenylsulphanyl)phenyl]carbamate were initially charged in a three-neck flask provided with a precision glass stirrer, a silvered Vigreux column and a distillation system. A reduced pressure of about 1 mbar was applied and the mixture was heated gradually to 168° C. At a top temperature of 143° C., first of all, 257 g of phenol were distilled off. Thereafter, a total of 592 g of crude product having an NCO content of 16.5% was obtained. The crude product was subjected to fine distillation at 1 mbar and top temperature 118-121° C. to obtain a total of 502 g of 2-phenylthiophenyl isocyanate.

Preparation of 2-biphenyl isocyanate

A three-neck flask with dropping funnel, precision glass stirrer and distillation attachment was initially charged with 1500 g of Desmodur 2460M and heated to 140° C. Then, within 50 minutes, 243.7 g of 2-aminobiphenyl were added and the reaction temperature was kept below 160° C. Subsequently, the product was distilled off under high vacuum (about 0.03 mbar), and 203.2 g of 2-biphenyl isocyanate, a clear liquid, were obtained.

Preparation of 1-isocyanato-2-{[3-(phenylsulphanyl)phenyl]sulphanyl}benzene 100 g of 2-{[3-(phenylsulphanyl)phenyl]sulphanyl}aniline (prepared as described in Advanced Synthesis & Catalysis (2009), 351(14+15), 2369-2378) and 0.1 g of tetrabutylammonium bromide were dissolved in 470 g of dichloromethane/water (1:1), and 49.1 g of potassium carbonate were added. At 10° C., 53.1 g of phenyl chloroformate were added dropwise to the vigorously stirred mixture. After the reaction had ended, 0.52 g of methanol was added and the mixture was stirred at room temperature for a further hour. The crude product was discharged onto 1 l of water and the aqueous phase was extracted three times with 500 ml each time of dichloromethane. The organic phases were dried and the solvent was distilled off under reduced pressure. This gave 133 g of phenyl (2-{[3-(phenylsulphanyl)phenyl]sulphanyl}phenyl)carbamate as a colourless solid.

100 g of phenyl (2-{[3-(phenylsulphanyl)phenyl]sulphanyl}phenyl)carbamate were initially charged in a Kugelrohr distillation apparatus and heated at 160° C. and 0.1 mbar. The phenol formed was discarded and 72 g of crude product were obtained. After distillation in a Kugelrohr distillation apparatus, 65.3 g of 1-isocyanato-2-{[3-(phenylsulphanyl)phenyl]sulphanyl}benzene were obtained as a colourless liquid.

Example 1

2-({[2-(Phenylsulphanyl)phenyl]carbamoyl}oxy) propyl acrylate

A three-neck flask with condenser, precision glass stirrer and nitrogen gas inlet was initially charged with 16.0 g of 2-phenylthiophenyl isocyanate, and the reaction vessel was purged with nitrogen and then heated to 80° C. Then 5 mg of 2,6-di-tert-butyl-4-methylphenol and 1 mg of Bochi-Kat 22 were added. After stirring for 15 minutes, 9.01 g of hydroxypropyl acrylate were added dropwise thereto within 20 minutes. The mixture was stirred for 18 hours and 2-({[2-(phenylsulphanyl)phenyl]carbamoyl}oxy)propyl acrylate was obtained as a clear liquid which no longer contained any isocyanate.

Example 2

2-({[2-(Phenylsulphanyl)phenyl]carbamoyl}oxy) ethyl acrylate

A three-neck flask with condenser, precision glass stirrer and air inlet was initially charged with 45.9 g of 2-phenylthiophenyl isocyanate, 13.5 mg of 2,6-di-tert-butyl-4-methylphenol and 33.8 g of dibutyltin dilaurate, then heated to 60° C., After stirring for 20 minutes, 21.6 g of hydroxyethyl acrylate were added dropwise thereto within 10 minutes. The mixture was stirred for 19 hours and a further 30 mg of dibutyltin dilaurate were added. After a further 32 hours, a further 1.08 g of hydroxyalkyl acrylate were added and, after stirring for a further 5 hours, 2-({[2-(phenylsulphanyl)phenyl]carbamoyl}oxy)ethyl acrylate was obtained as a clear liquid which no longer contained any isocyanate.

Example 3

2-[(Biphenyl-2-ylcarbamoyl)oxy]propyl acrylate

A three-neck flask with condenser, precision glass stirrer and air inlet was initially charged with 7.8 g of biphenyl 2-isocyanate and 2.6 mg of 2,6-di-test-butyl-4-methylphenol, and then heated to 60° C. Then, with gradual introduction of air, 5.2 g of hydroxypropyl acrylate were added dropwise thereto within 30 minutes. After 1.5 hours, 6.5 mg of dibutyltin dilaurate were added thereto. The mixture was stirred for 46 hours and 2-[(biphenyl-2-ylcarbamoyl)oxy]propyl acrylate was obtained as a clear liquid which no longer contained any isocyanate.

Example 4

2-[(Biphenyl-2-ylcarbamoyl)oxy]ethyl acrylate

A three-neck flask with condenser, precision glass stirrer and air inlet was initially charged with 7.8 g of biphenyl 2-isocyanate and 2.4 mg of 2,6-di-tert-butyl-4-methylphenol, and then heated to 60° C. Then, with gradual introduction of air, 4.3 g of 2-hydroxyethyl acrylate were added dropwise thereto within 30 minutes. After 1.5 hours, 6.1 mg of dibutyltin dilaurate were added thereto. The mixture was stirred for 70 hours and 2-[(biphenyl-2-ylcarbamoyl)oxy]ethyl acrylate was obtained as a clear liquid which no longer contained any isocyanate and crystallized gradually to give a solid having a melting range of 110-120° C.

Example 5

2-{[(2-{[3-(Phenylsulphanyl)phenyl]sulphanyl}phenyl)carbamoyl]oxy}ethyl acrylate A 100 ml round-bottom flask was initially charged with 0.01 g of 2,6-di-tert-butyl-4-methylphenol, 0.01 g of dibutyltin dilaurate and 7.50 g of 1-isocyanato-2-{[3-(phenylsulphonyl)phenyl]sulphanyl}benzene in 30 ml of ethyl acetate and heated to 60° C. Subsequently, 2.50 g of 2-hydroxyethyl acrylate were added dropwise and the mixture was still kept at 60° C. until the isocyanate content had fallen below 0.1%. This was followed by cooling and complete removal of the ethyl acetate under reduced pressure. The product was obtained as a partly crystalline solid.

Example 6

2-{[(2-{[3-(Phenylsulphanyl)phenyl]sulphanyl}phenyl)carbamoyl]oxy}propyl acrylate A 100 ml round-bottom flask was initially charged with 0.01 g of 2,6-di-tert-butyl-4-methylphenol, 0.01 g of dibutyltin dilaurate and 7.30 g of 1-isocyanato-2-{[3-(phenylsulphanyl)phenyl]sulphanyl}benzene in 30 ml of ethyl acetate and heated to 60° C. Subsequently, 2.70 g of hydroxypropyl acrylate were added dropwise and the mixture was still kept at 60° C. until the isocyanate content had fallen below 0.1%. This was followed by cooling and complete removal of the ethyl acetate under reduced pressure. The product was obtained as a partly crystalline solid.

Comparative Example A 2-({[3-(Methylsulphanyl)phenyl]carbamoyl}oxy) ethyl prop-2-enoate A 100 ml round-bottom flask was initially charged with 0.02 g of 2,6-di-tert-butyl-4-methylphenol, 0.01 g of dibutyltin dilaurate, 11.7 g of 3-(methylthio)phenyl isocyanate, and the mixture was heated to 60° C. Subsequently, 8.2 g of 2-hydroxyethyl acrylate were added dropwise and the mixture was still kept at 60° C. until the isocyanate content had fallen below 0.1%. This was followed by cooling. The product was obtained as a colourless liquid.

Urethane acrylate 1: Phosphorothioyltris(oxybenzene-4,1-diylcarbamoyloxyethane-2,1-diyl)triacrylate A 500 ml round-bottom flask was initially charged with 0.1 g of 2,6-di-tert-butyl-4-methylphenol, 0.05 g of dibutyltin dilaurate and 213.1 g of a 27% solution of tris(p-isocyanatophenyl)thiophosphate in ethyl acetate (Desmodur® RFE, product from Bayer MaterialScience AG, Leverkusen, Germany), which were heated to 60° C. Subsequently, 42.4 g of 2-hydroxyethyl acrylate were added dropwise and the mixture was still kept at 60° C. until the isocyanate content had fallen below 0.1%. This was followed by cooling and complete removal of the ethyl acetate under reduced pressure. The product was obtained as a partly crystalline solid.

Polyol Component:

A 1 l flask was initially charged with 0.037 g of Desmorapid® SO, 374.8 g of ε-caprolactone and 374.8 g of a difunctional polytetrahydrofuran polyether polyol, which were heated to 120° C. and kept at this temperature until the solids content (proportion of nonvolatile constituents) was 99.5% by weight or higher. Subsequently, the mixture was cooled and the product was obtained as a waxy solid.

Dye 1:

5.84 g of anhydrous sodium bis(2-ethylhexyl)sulphosuccinate were dissolved in 75 ml of ethyl acetate. 14.5 g of the dye Astrazon Rosa FG 200%, dissolved in 50 ml of water, were added. The aqueous phase was removed and the organic phase was stirred three times with 50 ml of fresh water at 50° C. and the aqueous phase was removed each time, the last time at room temperature. After the aqueous phase had been removed, the solvent was distilled off under reduced pressure and 8.6 g of 3H-indolium, 2-[2-[4-[(2-chloroethyl)methylamino]phenyl]ethenyl]-1,3,3-trimethyl-1,4-bis(2-ethylhexyl)sulphosuccinate [153952-28-4] were obtained as an oil of high viscosity.

Fluorinated urethane: bis(2,2,3,3,4,4,5,5,6,6,7,7-Dodecafluoroheptyl)-(2,2,4-trimethylhexane-1,6-diyl)biscarbamate A 6 l round-bottom flask was initially charged with 0.50 g of Desmorapid Z and 1200 g of trimethylhexamethylene diisocyanate, and the mixture was heated to 80° C. Subsequently, 3798 g of 1H,1H,7H-perfluoroheptan-1-ol were added dropwise and the mixture was still kept at 80° C. until the isocyanate content had fallen below 0.1%. This was followed by cooling. The product was obtained as a colourless oil.

Preparation of the Inventive and Noninventive Holographic Media (Examples I-VI and Comparative Example I)

7.90 g of the above-described polyol component were melted and mixed with 7.65 g of the particular writing monomer (writing monomer 1 to 6 and Comparative Example A), 2.57 g of the above-described urethane acrylate 1, 5.10 g of the above-described fluorinated urethane, 0.91 g of CGI 909, 0.232 g of dye 1, 0.230 g of BYK 310, 0.128 g of Fomrez UL 28 and 3.789 g of ethyl acetate, such that a clear solution was obtained. This was followed by addition of 1.50 g Desmodur® N 3900 and mixing again.

Then this solution was applied in a roll-to-roll coating system to a 36 μm-thick PET film, where the product was applied by means of a coating bar in a wet film thickness of 19 μm. With a drying temperature of 85° C. and a drying time of 5 minutes, the coated film was dried and then protected with a 40 μm-thick polyethylene film. Subsequently, this film was packaged with exclusion of light.

Determination of the Moisture Stability of the Holograms Which Were Recorded in the Inventive and Noninventive Media.

The media produced as described in the "Preparation of the inventive and noninventive holographic media" section were then tested for their holographic properties as follows using a measuring arrangement according to FIG. 4:

The beam of a laser (emission wavelength 532 nm) is expanded to a diameter of ~3-4 cm with the aid of an optional expanding lens (AF) and the collimation lens (CL) positioned after the shutter S. The diameter of the expanded laser beam is determined by the aperture of the open shutter. An inhomogeneous intensity distribution of the expanded laser beam is deliberately ensured. Thus, the edge intensity $P_R$ is ~ only half of the intensity $P_Z$ in the centre of the expanded laser beam. P should be understood here as power/area. The expanded laser beam at first passes through a glass plate placed at an oblique angle to the beam, which serves as shearing plate (SP). On the basis of the interference pattern reflected upward, which is produced by the two glass surface reflections of the SP, it is possible to see whether the laser emits in a stable manner in single mode. In that case, on an above the SP positioned diffusing screen composed of dark and light stripes is observed. Only when there is single mode emission are holographic exposures conducted. In the case of the DPSS laser, the single mode can be achieved by adjusting the pump power. The expanded beam passes through the holographic medium (P) at an oblique angle of about 15°; this portion forms the reference beam, in order then to be reflected by the object (O) arranged parallel to P back into P. This portion then forms the signal beam of the Denisyuk arrangement.

The interference of signal beam and reference beam in P creates the hologram in the holographic medium. O consists of a metal plate covered with white paper, with the paper side P facing forward. On the paper is a square pattern produced by black lines. The edge length of a square is 0.5 cm. This pattern is imaged in the hologram as well in the holographic exposure of P.

The mean exposure dose $E_{ave}$ is adjusted via the opening time t of S. With fixed laser power I, t is therefore the parameter proportional to $E_{ave}$. Since the expanded laser beam has an inhomogeneous (bell-shaped) intensity distribution, the local dose E for creation of the hologram in P varies. Together with the oblique arrangement of P and O relative to the optical axis, the effect of this is that the written hologram has an elliptical form. Since O is a diffuse reflector, the hologram is easily reconstructed by illumination with a point light source (e.g. pocket torch), and it is likewise possible to examine the holograms in the transmission mode of a UV-VIS spectrometer and compare them with one another.

Subsequently, the samples were placed onto the conveyor belt of a UV source with the substrate side facing the lamp and exposed twice at a belt speed of 2.5 m/min. The UV source used was an iron-doped Hg lamp of the Fusion UV type "D Bulb" No. 558434 KR 85 with total power density 80 W/cm$^2$. The parameters corresponded to a dose of 2×2.0 J/cm$^2$ (measured with an ILT 490 Light Bug).

The media thus obtained were examined in a UV-VIS spectrometer. For this purpose, a transmission measurement through the medium was conducted and recorded. Via the evaluation of the transmission curve, it is possible to determine the lowest transmission; this corresponds to the highest diffraction efficiency. Then the resonance frequency (in nm) in the transmission spectrum at the lowest transmission is determined and reported as $T_{min}$.

The transmission spectra of the written holograms of Inventive Examples 1-6 and Comparative Example A were determined thereafter. The media containing the holograms produced as described above were stored at various temperatures and air humidities and $T_{min}$ was determined again on completion of the storage.

Study of Thermal Stability:

The samples were stored at 100° C. In an oven for two days and cooled within 2 minutes, and $T_{min}(1)$ was determined. Subsequently, the samples were stored at about 20° C. and 40%-50% relative humidity for 7 days and $T_{min}(2)$ was determined. Finally, the difference in the peak wavelengths of the two measurements $\Delta T_{min}(1)$ was calculated.

Study of Moisture Stability:

The samples were stored at 60° C./95% relative air humidity for two days and cooled within 2 minutes, and $T_{min}(3)$ was determined. Subsequently, the samples were stored at about 20° C. and 40%-50% relative humidity for 7 days and $T_{min}(4)$ was determined. Finally, the difference in the peak wavelengths of the two measurements $\Delta T_{min}(2)$ was calculated.

Study of Holographic Performance (see Table 1)

The determination of the refractive index modulation Δn was conducted by the process described above in the "Test methods" section. Inventive Examples 1-6 and Comparative Example A show good holographic performance with a refractive index modulation Δn>0.025. In the study of thermal stability, a value of <2 nm $\Delta T_{min}(1)$ was consistently found. In the study of moisture stability, for the inventive examples, a value of <5 nm $\Delta T_{min}(2)$ was consistently found. The comparative example has a $\Delta T_{min}(2)$ of 7.4 nm. Thus, the inventive examples of the formula (I) have a maximum change in the reconstruction wavelength of less than 5 nm based on a reflection hologram which has been written by interference of two planar waves having a wavelength of 532 nm.

TABLE 1

| Unit | Δn — | $T_{min}$ [nm] | $T_{min}(1)$ [nm] | $T_{min}(2)$ [nm] | $\Delta T_{min}(1)$ [nm] | $T_{min}(3)$ [nm] | $T_{min}(4)$ [nm] | $\Delta T_{min}(2)$ [nm] |
|---|---|---|---|---|---|---|---|---|
| Example | | | | | | | | |
| 1 | 0.029 | 530.7 | 529.0 | 530.0 | −1.0 | 534.8 | 530.7 | 4.1 |
| 2 | 0.033 | 529.3 | 527.8 | 528.4 | −0.6 | 533.1 | 528.4 | 4.7 |
| 3 | 0.028 | 529.0 | 527.4 | 527.8 | −0.4 | 532.3 | 527.8 | 4.5 |
| 4 | 0.027 | 527.1 | 525.3 | 525.9 | −0.6 | 531.5 | 526.7 | 4.8 |
| 5 | 0.034 | 530.7 | 528.2 | 530.0 | −1.9 | 533.5 | 529.8 | 3.7 |
| 6 | 0.036 | 529.7 | 527.2 | 528.6 | −1.4 | 532.9 | 529.6 | 3.3 |

TABLE 1-continued

| Unit | Δn — | $T_{min}$ [nm] | $T_{min}(1)$ [nm] | $T_{min}(2)$ [nm] | $\Delta T_{min}(1)$ [nm] | $T_{min}(3)$ [nm] | $T_{min}(4)$ [nm] | $\Delta T_{min}(2)$ [nm] |
|---|---|---|---|---|---|---|---|---|
| Comparative Example | | | | | | | | |
| A | 0.033 | 526.9 | 524.5 | 525.1 | −0.6 | 532.7 | 525.3 | 7.4 |

The invention claimed is:

1. A photopolymer comprising matrix polymers, writing monomers and photoinitiators, wherein the writing monomers comprise compound of formula (I)

in which
R$^1$ is an aliphatic hydrocarbyl radical having 1-8 carbon atoms;
R$^2$ is hydrogen or methyl;
Ar is an aromatic radical of the formula (II)

in which
R$^3$ are independently radicals selected from the group of substituted or unsubstituted phenyl, substituted or unsubstituted phenylthiyl, branched or unbranched alkyl, branched or unbranched alkylthiyl, halogen, where at least one of the R$^3$ radicals is a radical selected from the group of substituted or unsubstituted phenyl, substituted or unsubstituted phenylthiyl;
n=1 to 5;
or Ar is an aromatic radical of the formula (III)

in which
R$^3$ are independently radicals selected from the group of substituted or unsubstituted phenyl, substituted or unsubstituted phenylthiyl, branched or unbranched alkyl, branched or unbranched alkylthiyl, halogen, where at least one of the R$^3$ radicals is a radical selected from the group of substituted or unsubstituted phenyl, substituted or unsubstituted phenylthiyl;
o=1 to 3;
p=1 to 4,
wherein the compound of the formula (I) has only one radiation-curing group, and wherein a reflection hologram comprising the photopolymer has a refractive index modulation of Δn>0.025 and value of $\Delta T_{min}(1)$ of <2 nm and a value $\Delta T_{min}(2)$ of <5 nm, wherein $\Delta T_{min}(1)$ is determined by first obtaining $T_{min}(1)$, the resonance frequency (in nm) in the transmission spectrum at the lowest transmission from a sample stored at 100° C. in an oven for two days and cooled within 2 minutes, subsequently obtaining $T_{min}(2)$ from a sample stored at about 20° C. and 40%-50% relative humidity for 7 days, and taking the difference in the peak wavelengths of the two measurements $T_{min}(1)$ and $T_{min}(2)$, and wherein $\Delta T_{min}(2)$ is determined by first obtaining $T_{min}(3)$ the resonance frequency (in nm) in the transmission spectrum at the lowest transmission from a sample stored at 60° C./95% relative air humidity for two days and cooled within 2 minutes, subsequently obtaining $T_{min}(4)$ from a sample stored at about 20° C. and 40%-50% relative humidity for 7 days, and taking the difference in the peak wavelengths of the two measurements $T_{min}(3)$ and $T_{min}(4)$.

2. The photopolymer according to claim 1, wherein at least one of the R$^3$ radicals is selected from the group of phenyl, phenylthiyl, phenylthiylphenylthiyl, alkylphenyl, alkylphenylthiyl, biphenyl.

3. The photopolymer according to claim 1, wherein Ar is a radical of the formula (II).

4. The photopolymer according to claim 1, wherein o=1.

5. The photopolymer according to claim 1, wherein R$^1$ is a radical selected from the group of —CH$_2$—CH$_2$—, —CH$_2$—CH$_2$—CH$_2$—, —CH$_2$—CHCH$_3$—, —CH$_2$—CH$_2$—CH$_2$—CH$_2$—.

6. The photopolymer according to claim 1, wherein the matrix polymers are crosslinked matrix polymers, preferably three-dimensionally crosslinked matrix polymers and most preferably are three-dimensionally crosslinked polyurethanes.

7. The photopolymer according to claim 1, wherein it comprises monomeric fluorourethanes.

8. A holographic medium comprising a photopolymer according to claim 1 which is coated as a film.

9. The holographic medium according to claim 8, wherein the film has a film thickness of 0.3 µm to 500 µm, more preferably with a film thickness of 0.5 µm to 200 µm and yet more preferably with a film thickness of 1 µm to 100 µm.

10. An optical display comprising a holographic medium according to claim 8.

11. A security document comprising a holographic medium according to claim 8.

12. A holographic optical element comprising a holographic medium according to claim 8.

13. A photopolymer comprising matrix polymers, writing monomers, monomeric fluorourethanes, and photoinitiators, wherein the writing monomers comprise compound of formula (I)

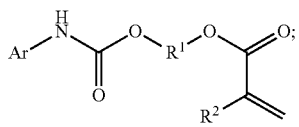

in which
R$^1$ is an aliphatic hydrocarbyl radical having 1-8 carbon atoms;
R$^2$ is hydrogen or methyl;
Ar is an aromatic radical of the formula (II)

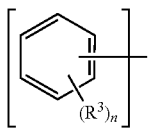

in which
R$^3$ are independently radicals selected from the group of substituted or unsubstituted phenyl, substituted or unsubstituted phenylthiyl, branched or unbranched alkyl, branched or unbranched alkylthiyl, halogen, where at least one of the R$^3$ radicals is a radical selected from the group of substituted or unsubstituted phenyl, substituted or unsubstituted phenylthiyl;
n=1 to 5;
or Ar is an aromatic radical of the formula (III)

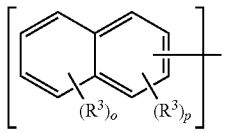

in which
R$^3$ are independently radicals selected from the group of substituted or unsubstituted phenyl, substituted or unsubstituted phenylthiyl, branched or unbranched alkyl, branched or unbranched alkylthiyl, halogen, where at least one of the R$^3$ radicals is a radical selected from the group of substituted or unsubstituted phenyl, substituted or unsubstituted phenylthiyl;
o=1 to 3;
p=1 to 4,
wherein the compound of the formula (I) has only one radiation-curing group and wherein a hologram comprising the photopolymer has a refractive index modulation of $\Delta n > 0.025$ and value of $\Delta T_{min}(1)$ of <2 nm and a value $\Delta T_{min}(2)$ of <5 nm, wherein $\Delta T_{min}(1)$ is determined by first obtaining $T_{min}(1)$, the resonance frequency (in nm) in the transmission spectrum at the lowest transmission from a sample stored at 100° C. in an oven for two days and cooled within 2 minutes, subsequently obtaining $T_{min}(2)$ from a sample stored at about 20° C. and 40%-50% relative humidity for 7 days, and taking the difference in the peak wavelengths of the two measurements $T_{min}(1)$ and $T_{min}(2)$, and wherein $\Delta T_{min}(2)$ is determined by first obtaining $T_{min}(3)$ the resonance frequency (in nm) in the transmission spectrum at the lowest transmission from a sample stored at 60° C./95% relative air humidity for two days and cooled within 2 minutes, subsequently obtaining $T_{min}(4)$ from a sample stored at about 20° C. and 40%-50% relative humidity for 7 days, and taking the difference in the peak wavelengths of the two measurements $T_{min}(3)$ and $T_{min}(4)$.

* * * * *